US010456052B2

(12) United States Patent
Lee

(10) Patent No.: US 10,456,052 B2
(45) Date of Patent: Oct. 29, 2019

(54) ELECTRONIC DEVICE HAVING SEGMENTAL PORTION ON HOUSING THEREOF

(71) Applicant: Samsung Electronics Co., Ltd., Gyeonggi-do (KR)

(72) Inventor: June Lee, Gyeonggi-do (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 0 days.

(21) Appl. No.: 15/422,763

(22) Filed: Feb. 2, 2017

(65) Prior Publication Data

US 2017/0245377 A1    Aug. 24, 2017

(30) Foreign Application Priority Data

Feb. 22, 2016    (KR) .................. 10-2016-0020359

(51) Int. Cl.
| | |
|---|---|
| *H05K 5/00* | (2006.01) |
| *A61B 5/024* | (2006.01) |
| *G01J 1/42* | (2006.01) |
| *G01J 1/44* | (2006.01) |
| *G01J 1/02* | (2006.01) |
| *H04M 1/02* | (2006.01) |
| *A61B 5/00* | (2006.01) |
| *A61B 5/0402* | (2006.01) |
| *A61B 5/053* | (2006.01) |
| *A61B 5/1172* | (2016.01) |
| *A61B 5/026* | (2006.01) |

(52) U.S. Cl.
CPC ........ *A61B 5/02416* (2013.01); *A61B 5/6898* (2013.01); *G01J 1/0271* (2013.01); *G01J 1/4204* (2013.01); *G01J 1/4228* (2013.01); *G01J 1/44* (2013.01); *H04M 1/0202* (2013.01); *H04M 1/0268* (2013.01); *A61B 5/0261* (2013.01); *A61B 5/0402* (2013.01); *A61B 5/0533* (2013.01); *A61B 5/1172* (2013.01); *H04M 1/0214* (2013.01); *H04M 1/0235* (2013.01)

(58) Field of Classification Search
CPC .................................................... G06F 1/1613
See application file for complete search history.

(56) References Cited

U.S. PATENT DOCUMENTS

| | | | |
|---|---|---|---|
| 2012/0112970 A1* | 5/2012 | Caballero | H01Q 1/243 343/702 |
| 2013/0063611 A1* | 3/2013 | Papakipos | G06F 1/1686 348/207.11 |
| 2014/0062801 A1 | 3/2014 | Yong et al. | |

* cited by examiner

*Primary Examiner* — Jerry Wu
(74) *Attorney, Agent, or Firm* — Cha & Reiter LLC.

(57) ABSTRACT

A housing of an electronic device may operate as an antenna while being partly insulated to prevent the degradation of antenna radiation efficiency. The electronic device may include a housing, a display, at least one sensor, and at least one processor. The housing may include a first surface, a second surface opposite to the first surface, and a side surface enclosing at least part of a space between the first and second surfaces. The side surface may include an elongated first member that is formed of an opaque material, and at least one second member dividing the first member into at least two segments and formed of a light-transmittable material. The at least one sensor may be located in the space adjacent to the at least one second member and oriented to detect incident light received through the at least one second member.

12 Claims, 24 Drawing Sheets

ELECTRONIC DEVICE HAVING SEGMENTAL PORTION ON HOUSING THEREOF

CLAIM OF PRIORITY

This application claims the benefit of priority under 35 U.S.C. § 119(a) from a Korean patent application filed on Feb. 22, 2016, in the Korean Intellectual Property Office and assigned Serial No. 10-2016-0020359, the entire disclosure of which is hereby incorporated by reference.

BACKGROUND

Field of the Disclosure

The present disclosure relates to an electronic device having a segmental portion on a housing thereof.

Description of the Related Art

With the growth of related technologies, a great variety of electronic devices are developed rapidly and used widely in various fields. For example, the electronic device becomes increasingly smaller for improved portability, and the ability to provide suitable services for various ubiquitous environments has also improved, while providing a traditional voice call wireless service.

Current wireless communication techniques require that the electronic device has includes an antenna for operation. Normally, the antenna of the electronic device is protrudable from a housing of the electronic device, or is embedded in the housing.

It is now common that the antenna of the electronic device is embedded in the housing formed of a metal frame. In this type of construction, a signal transmitted from the embedded antenna may be distorted or blocked due to the metal frame. Unfortunately, this may cause the degradation of the antenna's radiation efficiency.

Meanwhile, the housing of the electronic device has a limited inner space into which the antenna is mounted, and based on consumer demand for thinner electronic devices, the trend in reducing the thickness of devices such as smartphones and handheld tablets presents a serious challenge to arrange an antenna within the electronic devices. Additionally, in case of supporting various frequency bands, several antennas or an antenna having a complicated form is needed, and hence the housing inner space is further crowded.

SUMMARY

According to various embodiments of the present disclosure, a housing of an electronic device may have a portion operative as an antenna while being partly insulated. This construction can prevent the degradation of the antenna's radiation efficiency.

According to various embodiments of the present disclosure, an electronic device may include a housing, a display, at least one sensor, and a processor. The housing may include a first surface, a second surface being opposite to the first surface, and a side surface enclosing at least part of a space formed between the first and second surfaces. The side surface of the housing may include a first member elongated along the side surface and formed of an opaque material, and at least one second member dividing the first member into at least two segments and formed of a light-transmittable material. The display may be exposed on the first surface. The at least one sensor may be arranged in the space adjacent to the at least one second member and oriented to detect incident light received through the at least one second member. The processor may be electrically connected with the display and the sensor.

According to various embodiments of the present disclosure, an electronic device may include a housing, a display, a biometric sensor, and a processor. The housing may include a first surface, a second surface being opposite to the first surface, and a side surface enclosing at least part of a space formed between the first and second surfaces. The side surface of the housing may include a first member elongated along the side surface and divided into segments, a second member formed of a metallic material and located between the segments of the first member, a third member for electrically isolating one of the segments of the first member from the second member, and a fourth member for electrically isolating the other of the segments of the first member from the second member. The display may be exposed on the first surface. The biometric sensor may be arranged in the space and electrically connected with the second member. The processor may be electrically connected with the display and the biometric sensor.

According to various embodiments of the present disclosure, an operating method of an electronic device having at least one segmental portion may include obtaining information through a sensor equipped in the electronic device; recognizing a state of the electronic device, based on at least part of the obtained information; determining a presence of a luminance sensor located at a relatively upper position, based on at least part of the recognized state of the electronic device; detecting incident light through the segmental portion adjacent to the determined luminance sensor by controlling the determined luminance sensor; and determining ambient brightness around the electronic device, based on the detected light.

According to various embodiments of the present disclosure, the electronic device uses an insulated part of the housing as an optical sensor window or an electrode so as to enhance the performance of antenna.

DETAILED DESCRIPTION

Figure 1:
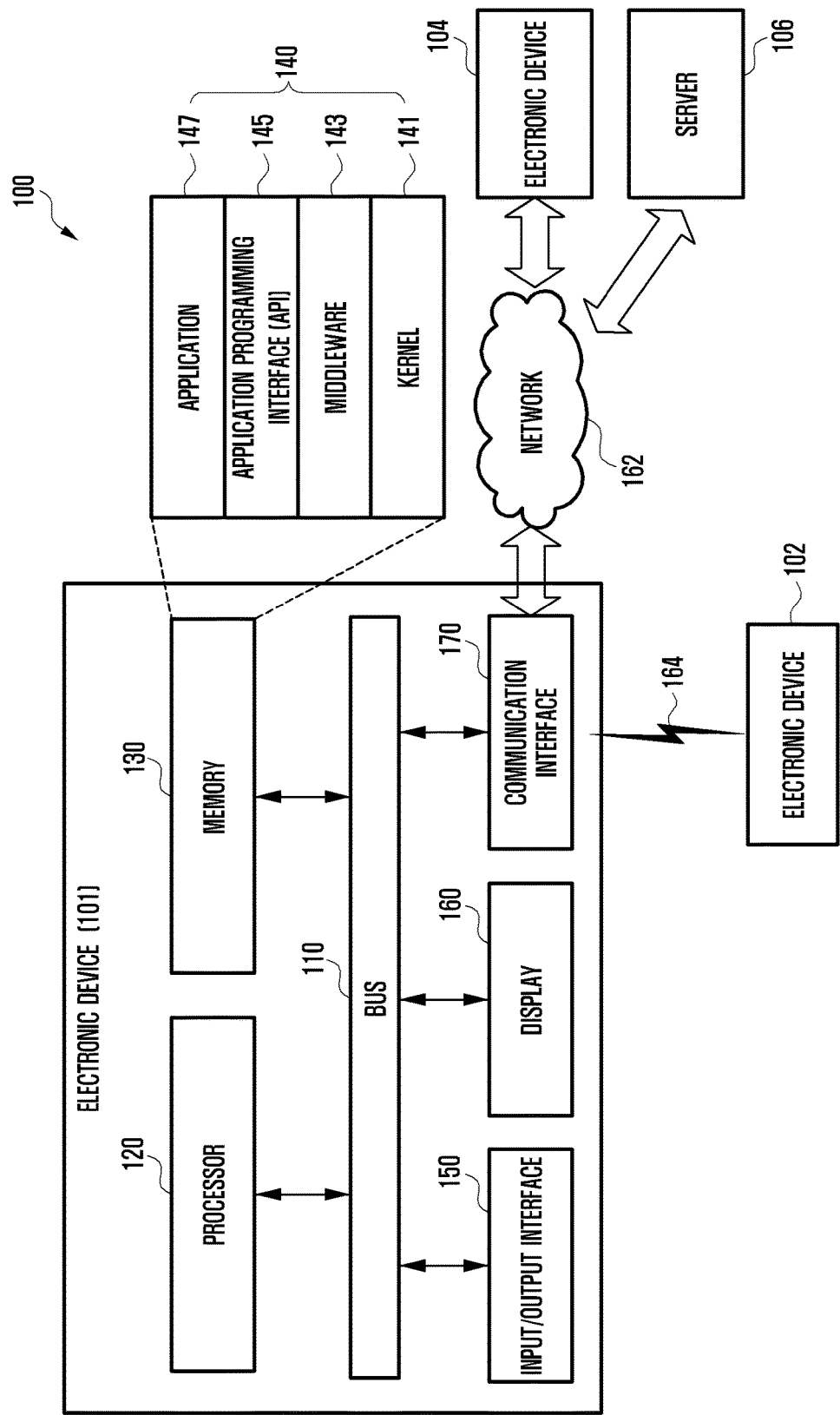
FIG. 1 is a block diagram illustrating an electronic device and a network environment according to various embodiments of the present disclosure.

Hereinafter, various embodiments of the present specification will be described with reference to the accompanying drawings. However, it should be understood by a person of ordinary skill in the art that there is no intent to limit the present disclosure to the particular forms disclosed herein; rather, the present disclosure should be construed to cover various modifications, equivalents, and/or alternatives of embodiments of the present disclosure. In describing the drawings, similar reference numerals may be used to designate similar constituent elements.

As used herein, the expressions "have", "may have", "include", or "may include" refer to the existence of a corresponding feature (e.g., numeral, function, operation, or constituent element such as component), and does not exclude one or more additional features.

In the present disclosure, the expression "A or B", "at least one of A or/and B", or "one or more of A or/and B" may include all possible combinations of the items listed. For example, the expression "A or B", "at least one of A and B", or "at least one of A or B" refers to all of (1) including at least one A, (2) including at least one B, or (3) including all of at least one A and at least one B.

The expression "a first", "a second", "the first", or "the second" used in various embodiments of the present disclosure may modify various components regardless of the order and/or the importance but does not limit the corresponding components. For example, a first user device and a second user device indicate different user devices although both of them are user devices. For example, a first element may be termed a second element, and similarly, a second element may be termed a first element without departing from the scope of the present disclosure.

It should be understood that when an element (e.g., first element) is referred to as being (operatively or communicatively) "connected," or "coupled," to another element (e.g., second element), it may be directly connected or coupled directly to the other element or any other element (e.g., third element) may be interposer between them. In contrast, it may be understood that when an element (e.g., first element) is referred to as being "directly connected," or "directly coupled" to another element (second element), there are no element (e.g., third element) interposed between them.

The expression "configured to" used in the present disclosure may be understood by an artisan to mean, for example, "suitable for", "having the capacity to", "designed to", "adapted to", or "made to", according to the situation. The term "configured to" may not necessarily imply "specifically designed to" in hardware. For example, the phrase "processor adapted (or configured) to perform A, B, and C" may mean a dedicated processor (e.g. embedded processor) only for performing the corresponding operations or a generic-purpose processor (e.g., central processing unit (CPU) or application processor (AP)) that can perform the corresponding operations by executing one or more software programs stored in a memory device.

The terms used in the present disclosure are only used to describe specific embodiments, and do not limit the attached claims. As used herein, singular forms may include plural forms as well unless the context clearly indicates otherwise. Unless defined otherwise, all terms used herein, including technical and scientific terms, have the same meaning as those commonly understood by a person skilled in the art to which the present disclosure pertains. Such terms as those defined in a generally used technical dictionary may be interpreted to have the meanings relevant to the contextual meanings in the relevant field of art, and are not to be interpreted to have ideal or excessively formal meanings unless clearly defined in the present disclosure. In some cases, even the term defined in the present disclosure should not be interpreted to exclude embodiments of the present disclosure.

In the present disclosure, an electronic device may be a device that involves a communication function. For example, an electronic device may be a smart phone, a tablet PC (Personal Computer), a mobile phone, a video phone, an e-book reader, a desktop PC, a laptop PC, a netbook computer, a PDA (Personal Digital Assistant), a PMP (Portable Multimedia Player), an MP3 player, a portable medical device, a digital camera, or a wearable device (e.g., an HMD (Head-Mounted Device) such as electronic glasses, electronic clothes, an electronic bracelet, an electronic necklace, an electronic accessory, an electronic tattoo, a smart mirror, or a smart watch).

According to some embodiments of the present disclosure, an electronic device may be a smart home appliance that involves a communication function. For example, an electronic device may be a TV, a DVD (Digital Video Disk) player, audio equipment, a refrigerator, an air conditioner, a vacuum cleaner, an oven, a microwave, a washing machine, an air cleaner, a set-top box, a TV box (e.g., Samsung HomeSync, Apple TV, Google TV, etc.), a game console, an electronic dictionary, an electronic key, a camcorder, or an electronic picture frame.

According to another embodiment of the present disclosure, the electronic device may include at least one of various medical devices (e.g., various portable medical measuring devices (a blood glucose monitoring device, a heart rate monitoring device, a blood pressure measuring device, a body temperature measuring device, etc.), a Magnetic Resonance Angiography (MRA), a Magnetic Resonance Imaging (MRI), a Computed Tomography (CT) machine, and an ultrasonic machine), a navigation device, a Global Positioning System (GPS) receiver, an Event Data Recorder (EDR), a Flight Data Recorder (FDR), a Vehicle Infotainment Devices, an electronic devices for a ship (e.g., a navigation device for a ship, and a gyro-compass), avionics, security devices, an automotive head unit, a robot for home or industry, an automatic teller's machine (ATM) in banks, point of sales (POS) in a shop, or Internet device of things (e.g., a light bulb, various sensors, electric or gas meter, a sprinkler device, a fire alarm, a thermostat, a streetlamp, a toaster, a sporting goods, a hot water tank, a heater, a boiler, etc.)

According to some embodiments of the present disclosure, an electronic device may be furniture or part of a building or construction having a communication function, an electronic board, an electronic signature receiving device, a projector, or various measuring instruments (e.g., a water meter, an electric meter, a gas meter, a wave meter, etc.). An electronic device disclosed herein may be one of the above-mentioned devices or any combination thereof.

Hereinafter, an electronic device according to various embodiments will be described with reference to the accompanying drawings. As used herein, the term "user" may indicate a person who uses an electronic device or a device (e.g., an artificial intelligence electronic device) that uses an electronic device FIG. 1 illustrates a network environment including an electronic device according to various embodiments of the present disclosure.

Referring now to FIG. 1, an electronic device 101, in a network environment 100, may include a bus 110, a processor 120, a non-transitory memory 130, an input/output interface 150, a display 160, and a communication interface 170. According to some embodiments, the electronic device 101 may omit at least one of the components or further include another component.

The bus 110 may be a circuit connecting the above-described components and transmitting communication (e.g., a control message) between the above-described components.

The processor 120 may include one or more of a central processing unit (CPU), an application processor (AP) or a communication processor (CP). For example, the processor 120 may control at least one component of the electronic device 101 and/or execute calculation relating to communication or data processing.

The memory 130, which is non-transitory, may include volatile and/or non-volatile memory. For example, the memory 130 may store command or data relating to at least one component of the electronic device 101. According to some embodiments, the memory may store software and/or program 140. For example, the program 140 may include a kernel 141, middleware 143, an application programming interface (API) 145, and/or an application 147 and so on. At least one portion of the kernel 141, the middleware 143 and the API 145 may be defined as operating system (OS).

The kernel 141 controls or manages system resources (e.g., the bus 110, the processor 120, or the memory 130) used for executing an operation or function implemented by the remaining other program, for example, the middleware 143, the API 145, or the application 147. Further, the kernel 141 provides an interface for accessing individual components of the electronic device 101 from the middleware 143, the API 145, or the application 147 to control or manage the components.

The middleware 143 performs a relay function of allowing the API 145 or the application 147 to communicate with the kernel 141 to exchange data. Further, in operation requests received from the application 147, the middleware 143 performs a control for the operation requests (e.g., scheduling or load balancing) by using a method of assigning a priority, by which system resources (e.g., the bus 110, the processor 120, the memory 130 and the like) of the electronic device 101 may be used, to the application 147.

The API 145 is an interface by which the application 147 may control a function provided by the kernel 141 or the middleware 142 and includes, for example, at least one interface or function (e.g., command) for a file control, a window control, image processing, or a character control.

The input/output interface 150 may be interface to transmit command or data inputted by a user or another external device to another component(s) of the electronic device 101. Further, the input/output interface 150 may output the command or data received from the another component(s) of the electronic device 101 to the user or the another external device.

The display 160 may include, for example, liquid crystal display (LCD), light emitting diode (LED), organic LED (OLED), or micro electro mechanical system (MEMS) display, or electronic paper display. The display 160 may display, for example, various contents (text, image, video, icon, or symbol, and so on) to a user. The display 160 may include a touch screen, and receive touch, gesture, approaching, or hovering input using a part of body of the user.

The communication interface 170 may set communication of the electronic device 101 and an external device (e.g., a first external device 102, a second external device 104, or a server 106). For example, the communication interface 170 may be connected with the network 162 through wireless communication or wire communication and communicate with the external device (e.g., a second external device 104 or server 106).

Wireless communication may use, as cellular communication protocol, at least one of LTE (long-term evolution), LTE-A (LTE Advance), CDMA (code division multiple access), WCDMA (wideband CDMA), UMTS (universal mobile telecommunications system), WiBro (Wireless Broadband), GSM (Global System for Mobile Communications), and the like, for example. A short-range communication 164 may include, for example, at least one of Wi-Fi, Bluetooth, Near Field Communication (NFC), Magnetic Secure Transmission or near field Magnetic data Stripe Transmission (MST), and Global Navigation Satellite System (GNSS), and the like.

An MST module is capable of generating pulses corresponding to transmission data using electromagnetic signals, so that the pulses can generate magnetic field signals. The electronic device 101 transmits the magnetic field signals to a point of sales (POS) terminal (reader). The POS terminal (reader) detects the magnetic field signal via an MST reader, transforms the detected magnetic field signal into an electrical signal, and thus restores the data.

The GNSS may include at least one of, for example, a Global Positioning System (GPS), a Global navigation satellite system (Glonass), a Beidou Navigation Satellite System (hereinafter, referred to as "Beidou"), and Galileo (European global satellite-based navigation system). Hereinafter, the "GPS" may be interchangeably used with the "GNSS" in the present disclosure. Wired communication may include, for example, at least one of USB (universal serial bus), HDMI (high definition multimedia interface), RS-232 (recommended standard-232), POTS (plain old telephone service), and the like. The network 162 may include telecommunication network, for example, at least one of a computer network (e.g., LAN or WAN), internet, and a telephone network.

Each of the first external device 102 and the second external device 104 may be same type or different type of device with the electronic device 101. According to some embodiments, the server 106 may include one or more group of servers. According to various embodiments, at least one portion of executions executed by the electronic device may be performed by one or more electronic devices (e.g., external electronic device 102, 104, or server 106). According to some embodiments, when the electronic device 101 should perform a function or service automatically, the electronic device 101 may request performing of at least one function to the another device (e.g., external electronic device 102, 104, or server 106). For the above, cloud computing technology, distributed computing technology, or client-server computing technology may be used, for example.

Figure 2:
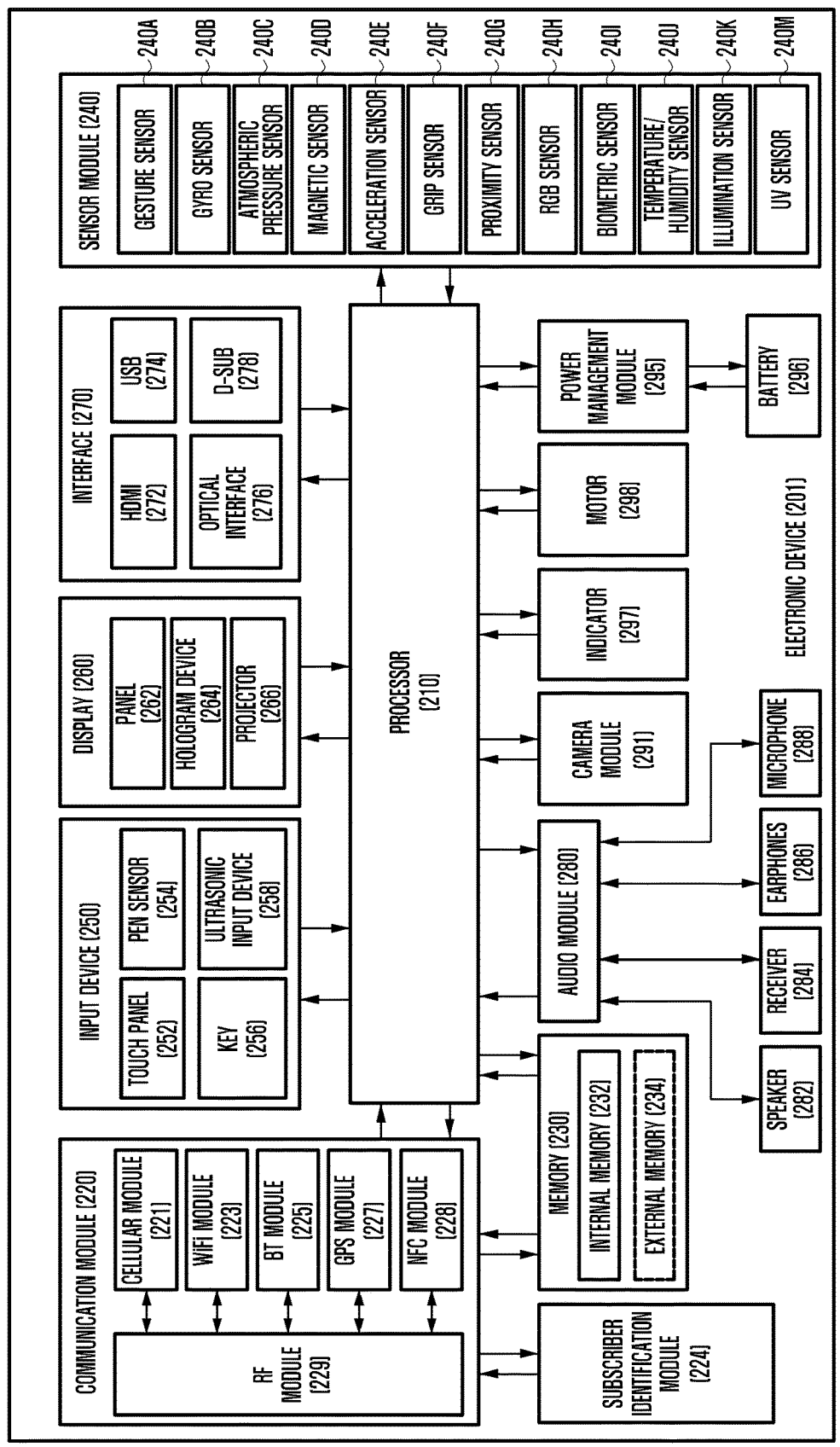
FIG. 2 is a block diagram illustrating an electronic device according to various embodiments of the present disclosure.

FIG. 2 illustrates a block diagram of an electronic device according to an embodiment of the present disclosure.

Referring now to FIG. 2, an electronic device 201 may configure, for example, a whole or a part of the electronic device 101 illustrated in FIG. 1. The electronic device 201 includes one or more APs 210, a communication module 220, a subscriber identification module (SIM) card 224, a memory 230, a sensor module 240, an input device 250, a display 260, an interface 270, an audio module 280, a camera module 291, a power managing module 295, a battery 296, an indicator 297, and a motor 298.

The AP 210 operates an OS or an application program so as to control a plurality of hardware or software component elements connected to the AP 210 and execute various data processing and calculations including multimedia data. The AP 210 may be implemented by, for example, a system-on-chip (SoC). According to an embodiment, the processor 210 may further include a graphics processing unit (GPU) and/or image signal processor. The AP 210 may include at least one portion of components illustrated in FIG. 2 (e.g., a cellular module 221). The AP 210 may load command or data received from at least one of another component (e.g., non-volatile memory), store various data in the non-volatile memory.

The communication module 220 may include the same or similar components with the communication interface 170 of FIG. 1. The communication module 220, for example, may include the cellular module 221, a Wi-Fi module 223, a BT module 225, a GPS module 227, a NFC module 228, and a radio frequency (RF) module 229.

The cellular module 221 provides a voice, a call, a video call, a short message service (SMS), or an internet service through a communication network (e.g., LTE, LTE-A, CDMA, WCDMA, UMTS, WiBro, GSM and the like). Further, the cellular module 221 may distinguish and authenticate electronic devices within a communication network by using a SIM (e.g., the SIM card 224). According to an embodiment, the cellular module 221 performs at least some of the functions which may be provided by the AP 210. For example, the cellular module 221 may perform at least some of the multimedia control functions. According to an embodiment of the present disclosure, the cellular module 221 may include a CP.

Each of the Wi-Fi module 223, the BT module 225, the GPS module 227, and the NFC module 228 may include, for example, a processor for processing data transmitted/received through the corresponding module. Although the cellular module 221, the Wi-Fi module 223, the BT module 225, the GPS module 227, and the NFC module 228 are at least some (e.g., two or more) of the cellular module 221, the Wi-Fi module 223, the BT module 225, the GPS module 227, and the NFC module 228 may be included in one integrated chip (IC) or one IC package according to one embodiment. For example, at least some (e.g., the CP corresponding to the cellular module 221 and the Wi-Fi processor corresponding to the Wi-Fi module 222 of the processors corresponding to the cellular module 221, the Wi-Fi module 223, the BT module 225, the GPS module 227, and the NFC module 228 may be implemented by one SoC.

The RF module 229 transmits/receives data, for example, an RF signal. Although not illustrated, the RF module 229 may include, for example, a transceiver, a power amp module (PAM), a frequency filter, a low noise amplifier (LNA) and the like. Further, the RF module 229 may further include a component for transmitting/receiving electronic waves over a free air space in wireless communication, for example, a conductor, a conducting wire, and the like. Although the cellular module 221, the Wi-Fi module 223, the BT module 225, the GPS module 227, and the NFC module 228 share one RF module 229 in FIG. 2, at least one of the cellular module 221, the Wi-Fi module 223, the BT module 225, the GPS module 227, and the NFC module 228 may transmit/receive an RF signal through a separate RF module according to one embodiment.

The SIM card 224 may be inserted into a slot formed in a particular portion of the electronic device. The SIM card 224 includes unique identification information (e.g., integrated circuit card identifier (ICCID)) or subscriber information (e.g., international mobile subscriber identity (IMSI).

The memory 230 (e.g., memory 130) may include an internal memory 232 or an external memory 234. The internal memory 232 may include, for example, at least one of a volatile memory (e.g., a random access memory (RAM), a dynamic RAM (DRAM), a static RAM (SRAM), a synchronous dynamic RAM (SDRAM), and the like), and a non-volatile Memory (e.g., a read only memory (ROM), a one time programmable ROM (OTPROM), a programmable ROM (PROM), an erasable and programmable ROM (EPROM), an electrically erasable and programmable ROM (EEPROM), a mask ROM, a flash ROM, a not and (NAND) flash memory, a not or (NOR) flash memory, and the like).

According to an embodiment, the internal memory 232 may be a solid state drive (SSD). The external memory 234 may further include a flash drive, for example, a compact flash (CF), a secure digital (SD), a micro-SD, a mini-SD, an extreme digital (xD), or a memory stick. The external memory 234 may be functionally connected to the electronic device 201 through various interfaces. According to an embodiment, the electronic device 201 may further include a storage device (or storage medium) such as a hard drive.

The sensor module 240 measures a physical quantity or detects an operation state of the electronic device 201, and converts the measured or detected information to an electronic signal. The sensor module 240 may include, for example, at least one of a gesture sensor 240A, a gyro sensor 240B, an atmospheric pressure (barometric) sensor 240C, a magnetic sensor 240D, an acceleration sensor 240E, a grip sensor 240F, a proximity sensor 240G, a color sensor 240H (e.g., red, green, and blue (RGB) sensor) 240H, a biometric sensor 240I, a temperature/humidity sensor 240J, an illumination (light) sensor 240K, and a ultraviolet (UV) sensor 240M. Additionally or alternatively, the sensor module 240 may include, for example, an E-nose sensor, an electromyography (EMG) sensor, an electroencephalogram (EEG) sensor, an electrocardiogram (ECG) sensor, an infrared (IR) sensor, an iris sensor, a fingerprint sensor (not illustrated), and the like. The sensor module 240 may further include a control circuit for controlling one or more sensors included in the sensor module 240.

The input device 250 includes a touch panel 252, a (digital) pen sensor 254, a key 256, and an ultrasonic input device 258. For example, the touch panel 252 may recognize a touch input in at least one type of a capacitive type, a resistive type, an infrared type, and an acoustic wave type. The touch panel 252 may further include a control circuit. In the capacitive type, the touch panel 252 may recognize proximity as well as a direct touch. The touch panel 252 may further include a tactile layer. In this event, the touch panel 252 provides a tactile reaction to the user.

The (digital) pen sensor 254 may be implemented, for example, using a method identical or similar to a method of receiving a touch input of the user, or using a separate recognition sheet. The key 256 may include, for example, a physical button, an optical key, or a key pad. The ultrasonic input device 258 is a device which may detect an acoustic wave by a microphone (e.g., a microphone 288) of the electronic device 201 through an input means generating an ultrasonic signal to identify data and may perform wireless recognition. According to an embodiment, the electronic device 201 receives a user input from an external device (e.g., computer or server) connected to the electronic device 201 by using the communication module 220.

The display 260 (e.g., display 160) includes a panel 262, a hologram device 264, and a projector 266. The panel 262 may be, for example, a LCD or an active matrix OLED (AM-OLED). The panel 262 may be implemented to be, for example, flexible, transparent, or wearable. The panel 262 may be configured by the touch panel 252 and one module. The hologram device 264 shows a stereoscopic image in the air by using interference of light. The projector 266 projects light on a screen to display an image. For example, the screen may be located inside or outside the electronic device 201. According to an embodiment, the display 260 may further include a control circuit for controlling the panel 262, the hologram device 264, and the projector 266.

The interface 270 includes, for example, a HDMI 272, an USB 274, an optical interface 276, and a D-subminiature (D-sub) 278. The interface 270 may be included in, for example, the communication interface 170 illustrated in FIG. 1. Additionally or alternatively, the interface 270 may include, for example, a mobile high-definition link (MHL) interface, an SD card/multi-media card (MMC), or an infrared data association (IrDA) standard interface.

The audio module 280 bi-directionally converts a sound and an electronic signal. At least some components of the audio module 280 may be included in, for example, the input/output interface 150 illustrated in FIG. 1. The audio module 280 processes sound information input or output through, for example, a speaker 282, a receiver 284, an earphone 286, the microphone 288 and the like.

The camera module 291 is a device which may photograph a still image and a video. According to an embodiment of the present disclosure, the camera module 291 may include one or more image sensors (e.g., a front sensor or a back sensor), an image signal processor (ISP) (not shown) or a flash (e.g., an LED or xenon lamp).

The power managing module 295 manages power of the electronic device 201. Although not illustrated, the power managing module 295 may include, for example, a power management integrated circuit (PMIC), a charger IC, or a battery or fuel gauge.

The PMIC may be mounted to, for example, an integrated circuit or a SoC semiconductor. A charging method may be divided into wired and wireless methods. The charger IC charges a battery and prevent over voltage or over current from flowing from a charger. According to an embodiment, the charger IC includes a charger IC for at least one of the wired charging method and the wireless charging method. The wireless charging method may include, for example, a magnetic resonance method, a magnetic induction method and an electromagnetic wave method, and additional circuits for wireless charging, for example, circuits such as a coil loop, a resonant circuit, a rectifier and the like may be added.

The battery fuel gauge measures, for example, a remaining quantity of the battery 296, or a voltage, a current, or a temperature during charging. The battery 296 may store or generate electricity and supply power to the electronic device 201 by using the stored or generated electricity. The battery 296 may include a rechargeable battery or a solar battery.

The indicator 297 shows particular statuses of the electronic device 201 or a part (e.g., AP 210) of the electronic device 201, for example, a booting status, a message status, a charging status and the like. The motor 298 converts an electrical signal to a mechanical vibration. Although not illustrated, the electronic device 201 may include a processing unit (e.g., GPU) for supporting a module TV. The processing unit for supporting the mobile TV may process, for example, media data according to a standard of digital multimedia broadcasting (DMB), digital video broadcasting (DVB), media flow and the like.

Each of the components of the electronic device according to various embodiments of the present disclosure may be implemented by one or more components and the name of the corresponding component may vary depending on a type of the electronic device. The electronic device according to various embodiments of the present disclosure may include at least one of the above described components, a few of the components may be omitted, or additional components may be further included. Also, some of the components of the electronic device according to various embodiments of the present disclosure may be combined to form a single entity, and thus may equivalently execute functions of the corresponding components before being combined.

Figure 3:
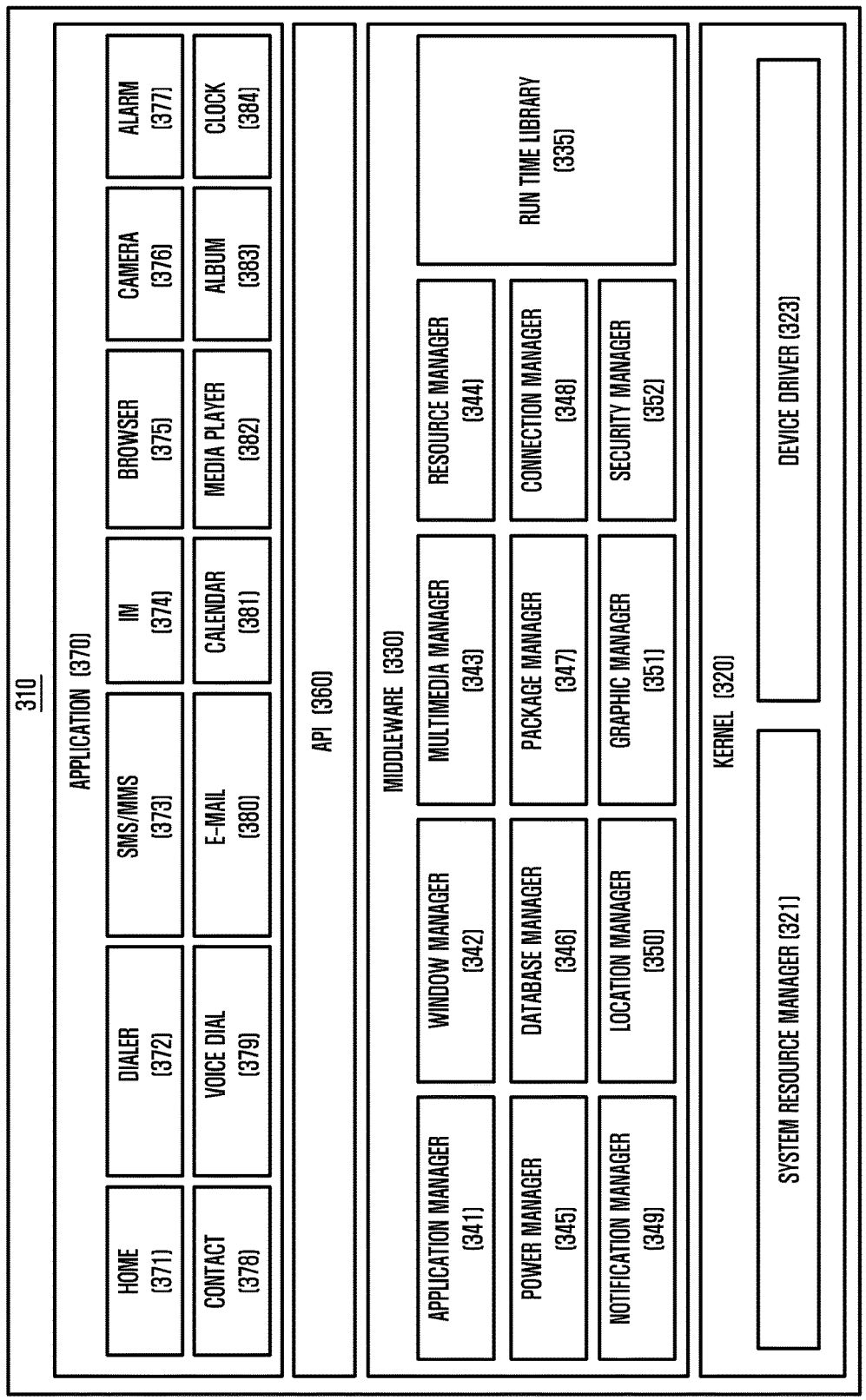
FIG. 3 is a block diagram illustrating a program module according to various embodiments of the present disclosure.

FIG. 3 is a block diagram illustrating a programming module according to an embodiment of the present disclosure.

Referring now to FIG. 3, a programming module 310 may be included, e.g. stored, in the electronic apparatus 101, e.g. the memory 130, as illustrated in FIG. 1. At least a part of the programming module 310 (e.g., program 147) may be configured by software, firmware, hardware, and/or combinations of two or more thereof. The programming module 310 may include an OS that is implemented in hardware, e.g., the hardware 200 to control resources related to an electronic device, e.g., the electronic device 100, and/or various applications. e.g., applications 370, driven on the OS. For example, the OS may be Android, iOS, Windows, Symbian, Tizen, Bada, and the like. Referring to FIG. 3, the programming module 310 may include a kernel 320, middleware 330, an API 360, and the applications 370 (e.g., application 147). At least part of the program module 310 may be preloaded on the electronic device or downloaded from a server (e.g., an electronic device 102, 104, server 106, etc.).

The kernel 320, which may be like the kernel 141, may include a system resource manager 321 and/or a device driver 323. The system resource manager 321 may include, for example, a process manager, a memory manager, and a file system manager. The system resource manager 321 may control, allocate, and/or collect system resources. The device driver 323 may include, for example, a display driver, a camera driver, a BT driver, a shared memory driver, a USB driver, a keypad driver, a Wi-Fi driver, and an audio driver. Further, according to an embodiment, the device driver 323 may include an inter-process communication (IPC) driver (not illustrated).

The middleware 330 may include a plurality of modules implemented in advance for providing functions commonly used by the applications 370. Further, the middleware 330 may provide the functions through the API 360 such that the applications 370 may efficiently use restricted system resources within the electronic apparatus. For example, as shown in FIG. 3, the middleware 330 may include at least one of a runtime library 335, an application manager 341, a window manager 342, a multimedia manager 343, a resource manager 344, a power manager 345, a database manager 346, a package manager 347, a connectivity manager 348, a notification manager 349, a location manager 350, a graphic manager 351, a security manager 352 and a payment manager 354.

The runtime library 335 may include a library module that a compiler uses in order to add a new function through a programming language while one of the applications 370 is being executed. According to an embodiment of the present disclosure, the runtime library 335 may perform an input/output, memory management, and/or a function for an arithmetic function.

The application manager 341 may manage a life cycle of at least one of the applications 370. The window manager 342 may manage graphical user interface (GUI) resources used by a screen. The multimedia manager 343 may detect formats used for reproduction of various media files, and may perform encoding and/or decoding of a media file by using a codec suitable for the corresponding format. The resource manager 344 may manage resources such as a source code, a memory, and a storage space of at least one of the applications 370.

The power manager 345 may manage a battery and/or power, while operating together with a basic input/output system (BIOS), and may provide power information used for operation. The database manager 346 may manage generation, search, and/or change of a database to be used by at least one of the applications 370. The package manager 347 may manage installation and/or an update of an application distributed in a form of a package file.

For example, the connectivity manager 348 may manage wireless connectivity such as Wi-Fi or BT. The notification manager 349 may display and/or notify of an event, such as an arrival message, a promise, a proximity notification, and the like, in such a way that does not disturb a user. The location manager 350 may manage location information of an electronic apparatus. The graphic manager 351 may manage a graphic effect which will be provided to a user, and/or a user interface related to the graphic effect. The security manager 352 may provide all security functions used for system security and/or user authentication. According to an embodiment, when an electronic apparatus, e.g., the electronic apparatus 100, has a telephone call function, the middleware 330 may further include a telephony manager (not illustrated) for managing a voice and/or video communication function of the electronic apparatus. The payment manger 354 is capable of relaying payment information from the application 370 to an application 370 or a kernel 320. Alternatively, the payment manager 354 is capable of storing payment-related information received from an external device in the electronic device 200 or transmitting information stored in the electronic device 200 to an external device.

The middleware 330 may generate and use a new middleware module through various functional combinations of the aforementioned internal element modules. The middleware 330 may provide modules specialized according to types of OSs in order to provide differentiated functions. Further, the middleware 330 may dynamically remove some of the existing elements and/or add new elements. Accordingly, the middleware 330 may exclude some of the elements described in the various embodiments of the present disclosure, further include other elements, and/or substitute the elements with elements having a different name and performing a similar function.

The API 360, which may be similar to the API 133, is a set of API programming functions, and may be provided with a different configuration according to the OS. For example, in a case of Android or iOS, one API set may be provided for each of platforms, and in a case of Tizen, two or more API sets may be provided.

The applications 370, which may include an application similar to the application 147, may include, for example, a preloaded application and/or a third party application. The applications 370 may include one or more of the following: a home application 371 a dialer application 372, an SMS/multimedia messaging service (MMS) application 373, an instant messaging (IM) application 374, a browser application 375, a camera application 376, an alarm application 377, a contact application 378, a voice dial application 379, an email application 380, a calendar application 381, a media player application 382, an album application 383, a clock application 384, a payment application 385, a health care application (e.g., the measurement of blood pressure, exercise intensity, etc.), an application for providing environment information (e.g., atmospheric pressure, humidity, temperature, etc.), etc. However, the present embodiment is not limited thereto, and the applications 370 may include any other similar and/or suitable application.

According to an embodiment of the present disclosure, the applications 370 are capable of including an application for supporting information exchange between an electronic device (e.g., electronic device 101) and an external device (e.g., electronic devices 102 and 104), which is hereafter called 'information exchange application'). The information exchange application is capable of including a notification relay application for relaying specific information to external devices or a device management application for managing external devices.

For example, the notification relay application is capable of including a function for relaying notification information, created in other applications of the electronic device (e.g., SMS/MMS application, email application, health care application, environment information application, etc.) to external devices (e.g., electronic devices 102 and 104). In addition, the notification relay application is capable of receiving notification information from external devices to provide the received information to the user.

The device management application is capable of managing (e.g., installing, removing or updating) at least one function of an external device (e.g., electronic devices 102 and 104) communicating with the electronic device. Examples of the function are a function of turning-on/off the external device or part of the external device, a function of controlling the brightness (or resolution) of the display, applications running on the external device, services provided by the external device, etc. Examples of the services are a call service, messaging service, etc.

According to an embodiment of the present disclosure, the applications 370 are capable of including an application (e.g., a health care application of a mobile medical device, etc.) specified attributes of an external device (e.g., electronic devices 102 and 104). According to an embodiment of the present disclosure, the applications 370 are capable of including applications received from an external device (e.g., a server 106, electronic devices 102 and 104). According to an embodiment, the applications 370 are capable of including a preloaded application or third party applications that can be downloaded from a server. It should be understood that the components of the program module 310 may be called different names according to types of operating systems.

According to various embodiments of the present disclosure, at least part of the program module 310 can be implemented with software, firmware, hardware, or any combination of two or more of them. At least part of the program module 310 can be implemented (e.g., executed) by a processor (e.g., processor 210). At least part of the programming module 310 may include modules, programs, routines, sets of instructions or processes, etc., in order to perform one or more functions.

FIGS. 4A to 4D are perspective views illustrating an electronic device 400 according to various embodiments of the present disclosure. The electronic device 400 shown in FIGS. 4A to 4D may be the electronic device 101 as shown in FIG. 1.

Figure 4A:
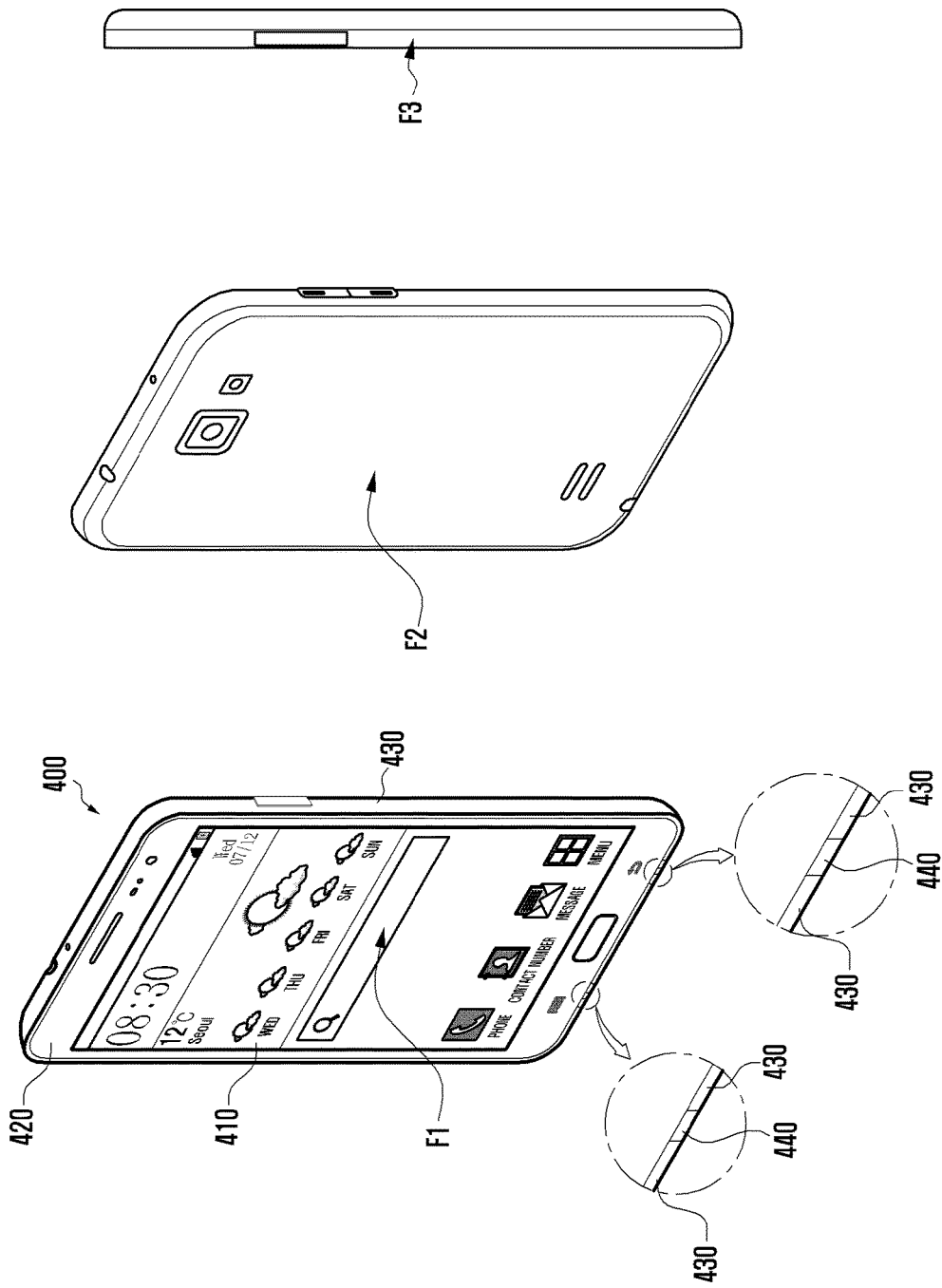
FIG. 4A is a perspective view illustrating an electronic device according to various embodiments of the present disclosure.

FIG. 4A shows the outward appearance of the electronic device 400. Referring to FIG. 4A, a housing of the electronic device 400 may include a first surface F1, a second surface F2 which is opposite to the first surface F1, and a side surface F3 which encloses at least part of a space formed between the first and second surfaces F1 and F2.

According to various embodiments of the present disclosure, a display 410 may be exposed at least partially on the first surface F1 of the housing. The display 410 may include, for example, a touch screen or a touch panel that performs both an image display function and a touch-based input function. A speaker, a sensor, a camera, a key button, etc. may be exposed on a partial region 420 of the first surface F1 to which the display 410 is not exposed. According to various embodiments of the present disclosure, another camera, another sensor, a flash, etc. may be exposed on the second surface F2 which is opposite to the first surface F1. A partial region of the second surface F2 to which the camera, the sensor, the flash, etc. that are not exposed may be formed of an opaque material (e.g., metal, plastic, glass, leather, etc.). Alternatively or additionally, a partial region of the second surface F2 may be formed of a transparent material (e.g., glass, etc.) such that the inner structure of the electronic device 400 can be seen at least partially. Although not shown, another display may be exposed at least partially on the second surface F2. For example, the camera, the sensor, the flash, etc. may be exposed on a partial region of the second surface F2 on which another display is not exposed. In a certain embodiment, the display 410 exposed on the first surface F1 and another display exposed on the second surface F2 may be configured in a transparent form. In this case, a user can see opposite objects through the display exposed on the first surface or the second surface.

According to various embodiments of the present disclosure, the side surface F3, which encloses at least part of a space formed between the first and second surfaces F1 and F2, may include a first member 430 formed of an opaque material. The first member may be a metallic member including at least one of, e.g., copper, silver, and aluminum. If the side surface F3 of the housing is formed of a metallic member, the metallic member may perform an antenna function. In various embodiments, in order to allow the side surface F3 to perform the antenna function, the side surface F3 may include a partially segmented (segmental) portion. Specifically, the electronic device 400 may include the first member 430 elongated along the side surface F3, and at least one segmental portion which divides the first member 430 into at least two segments and is located between the divided first members 430.

According to various embodiments of the present disclosure, the segmental portion may be filled with a second member 440. The second member 440 located in the segmental portion may be comprised of a nonmetallic member having an insulating property. For example, the second member 440 may be a nonmetallic member including but not limited to at least one of plastic resin, glass, and their equivalents.

According to various embodiments of the present disclosure, the side surface F3 of the housing may include one or more second members 440 depending on the number of the segmental portions. For example, if the side surface F3 of the housing has four segmental portions, the second member 440 may be located in each of the four segmental portions. The location of the segmental portion may be varied depending on a frequency band supported by the antenna or a shape of the electronic device 400.

According to various embodiments of the present disclosure, the second member 440 may be formed in the segmental portion through an injection molding process. For example, a nonmetallic material to be used as the second member 440 is injected into a mold, then cured, and combined with the first member 430 formed of a metallic material. Through this process, the second member 440 may be located in the segmental portion of the housing.

According to a certain embodiment of the present disclosure, the second surface F2 and the side surface F3 of the housing may be formed integrally, thus forming an unclear boundary between the second and side surfaces F2 and F3. For example, if the boundary between the second surface F2 and side surface F3 forms a curved surface, the boundary between the second e surface F2 and side surface F3 may be unclear. In this case, the second surface and side surface may include together the first member formed of an opaque material.

Additionally, in a certain embodiment of the present disclosure, the second surface F2 of the housing may also include a segmental portion. For example, if the boundary between the second surface F2 and side surface F3 forms a curved surface with an unclear boundary, the segmental portion formed on the side surface F3 may be continued to the second surface F2.

According to various embodiment of the present disclosure, the side surface F3 of the housing may include a first member elongated along the side surface F3 that is divided into two segments, a second member formed of a metallic material and located between the two segments of the first member, a third member for electrically isolating one of the two segments of the first member from the second member, and a fourth member for electrically isolating the other of the two segments of the first member from the second member.

Figure 4B:
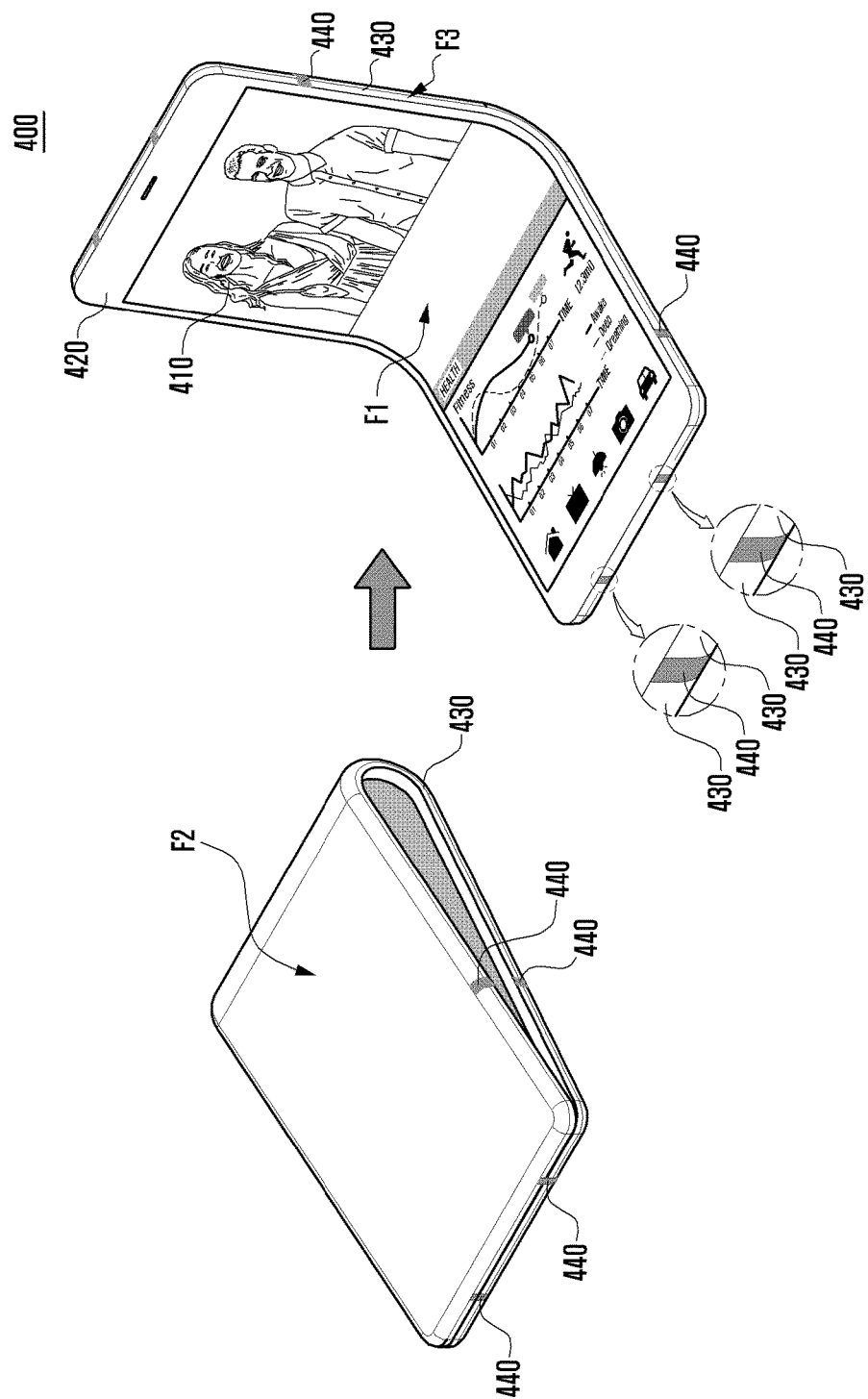
FIG. 4B is a perspective view illustrating an electronic device including a flexible display according to various embodiments of the present disclosure.

FIG. 4B is a perspective view illustrating an electronic device 400 including a flexible display according to various embodiments of the present disclosure. Referring to FIG. 4B, a housing of the electronic device 400 having the flexible display may include a first surface F1, a second surface F2 which is opposite to the first surface F1, and a side surface F3 which encloses at least part of a space formed between the first and second surfaces F1 and F2.

At least part of the first and second surfaces F1 and F2 may be formed of a metallic material or a nonmetallic hard material. The side surface F3 may include a first member having ductility.

According to various embodiments of the present disclosure, in order to allow the side surface F3 of the electronic device 400 having the flexible display to perform the antenna function, the side surface F3 may include partly a segmental portion. Specifically, the electronic device 400 having the flexible display may include the first member 430 elongated along the side surface F3, and at least one segmental portion which divides the first member 430 into at least two segments and is located between the divided first members 430.

According to various embodiments of the present disclosure, the segmental portion may be filled with a second member 440. The second member 440 located in the segmental portion may be a nonmetallic member having an insulation property. For example, the second member 440 may be a nonmetallic member including at least but not limited to one of plastic resin, glass, and their equivalents.

Figure 4C:
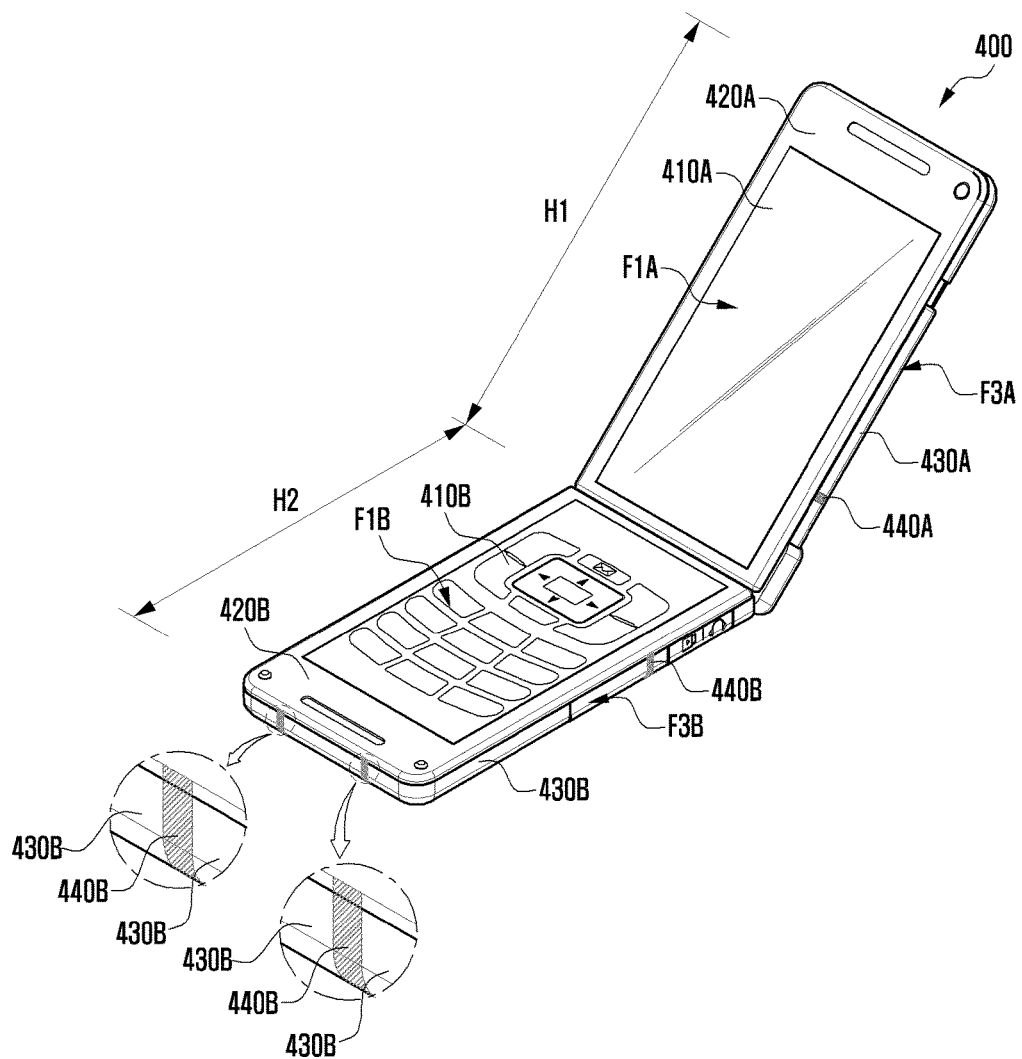
FIG. 4C is a perspective view illustrating an electronic device having two housings in which a first housing is directly or indirectly mechanically combined with a second housing according to various embodiments of the present disclosure.
Figure 4D:
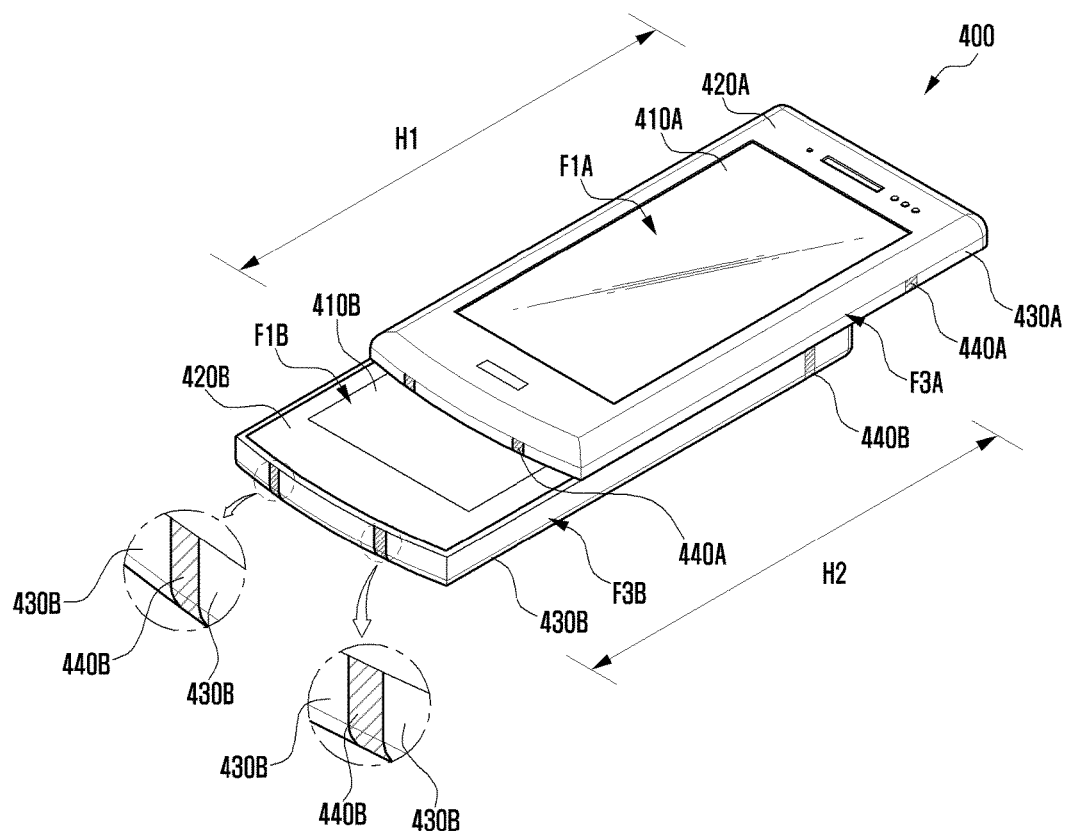
FIG. 4D is a perspective view of a second surface of a first housing being connected movably with a first surface of the second housing according to various embodiments of the present disclosure.

FIGS. 4C and 4D are perspective views illustrating an electronic device 400 having two housings, each of which includes a first surface, a second surface and a side surface according to various embodiments.

Referring to FIGS. 4C and 4D, a first housing H1 of the electronic device 400 may include a first surface F1A, a second surface F2A that is opposite to the first surface F1A, and a side surface F3A which encloses at least part of a space formed between the first and second surfaces F1A and F2A. The first housing H1 may have a directly or indirectly mechanical combination with a second housing H2 which includes another first surface F1B, another second surface F2B which is opposite to the another first surface F1B, and another side surface F3B which encloses at least part of a space formed between the another first and second surfaces F1B and F2B. For example, at least part of the first and second housings H1 and H2 may be combined with each other directly or indirectly using at least one connecting member.

According to various embodiments of the present disclosure, the electronic components in the first housing H1 and electronic components in the second housing H2 may be electrically connected with each other. For example, a printed circuit board (PCB) in the first housing H1 and a PCB of the second housing H2 may be electrically connected with each other through an electric wire or the like. Referring to FIG. 4C, one end of the side surface F3A of the first housing H1 and one end of the side surface F3B of the second housing H2 may be mechanically combined with each other. In this case, the electronic device 400 has the ability to be folded on a pivot between the first and second housings H1 and H2. This folder type electronic device is well known in the art, so that a detailed description will be omitted.

Referring now to FIG. 4D, the second surface F2A of the first housing H1 may be movably connected with the first surface F1B of the second housing H2. In this case, the electronic device 400 has the ability to slide the first housing H1 with regard to the second housing H2. This slider type electronic device is well known in the art, so that a detailed description will be omitted.

According to various embodiments of the present disclosure, the first surface F1B of the second housing H2 shown in FIGS. 4C and 4D may be configured to expose a keypad or a display thereon.

Referring now to FIGS. 4C and 4D, at least one of the side surfaces F3A and F3B of the electronic device 400 may include the first member 430A or 430B formed of an opaque material. The first member 430A or 430B formed of an opaque material may be a metallic member including at least one of, e.g., copper, silver, and aluminum. If the at least one side surface F3A or F3B is formed of a metallic member, the metallic member may perform an antenna function.

According to various embodiments of the present disclosure, in order to allow the at least one side surface F3A or F3B to perform the antenna function, the side surface F3A or F3B may include partly a segmental portion. Specifically, the electronic device 400 may include the first member 430A or 430B elongated along the side surface F3A or F3B, and at least one segmental portion which divides the first member 430A or 430B into at least two segments and is located between the divided first members 430A or 430B.

According to various embodiments of the present disclosure, the segmental portion may be filled with the second member 440A or 440B. The second member 440A or 440B located in the segmental portion may be a nonmetallic member having an insulation property. For example, the second member 440A or 440B may be a nonmetallic member including but not limited to at least one of plastic resin, glass, and their equivalents.

According to various embodiments of the present disclosure, the electronic device 400 having at least two housings may be configured for the corresponding segmental portion of each housing to be formed at a corresponding location when the housings are combined. For example, when the housings of the electronic device 400 shown in FIG. 4C or 4D is overlapped with each other, the corresponding segmental portions 440A and 440B formed in the respective housings may be placed at the same location.

Figure 5:
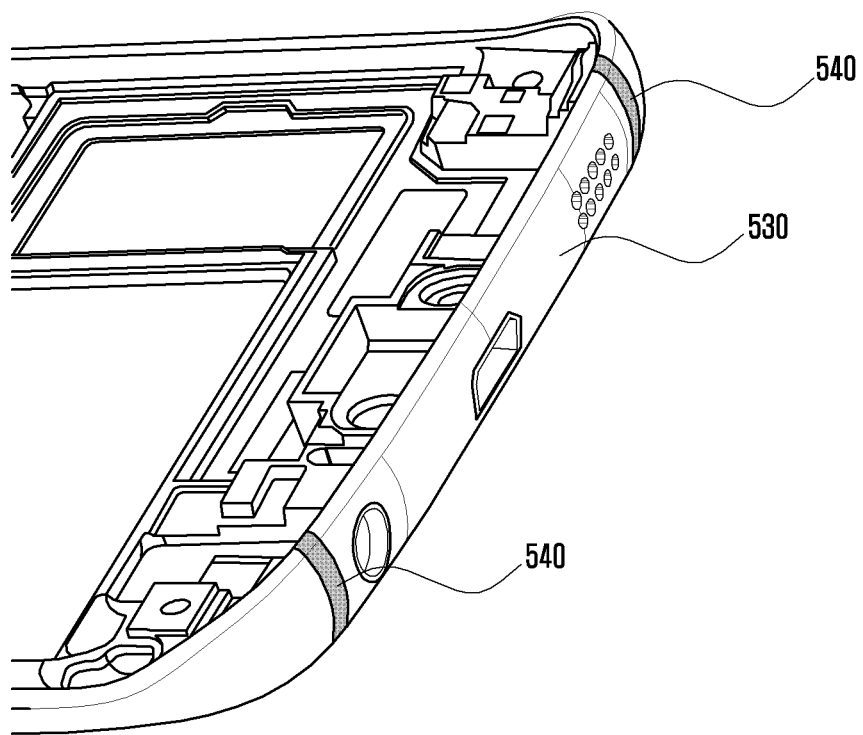
FIG. 5 is a perspective view partially illustrating a housing of an electronic device according to various embodiments of the present disclosure.

FIG. 5 is a perspective view partially illustrating a housing of an electronic device according to various embodiments.

Referring now to FIG. 5, the housing of the electronic device may include a first member 530 elongated along the side surface F3 and formed of an opaque material. The first member 530 formed of an opaque material may be a metallic member such as copper, silver, aluminum, or the like.

According to various embodiments of the present disclosure, the first member 530 may include a metallic member such as copper, silver or aluminum, and operate at least partly as an antenna radiator. For example, at least part of the first member 530 may be divided into at least two segments, thus including a segmental portion, so as to have a length corresponding to a supportable frequency band. The segmental portion may include the second member 540 formed of a nonmetallic member.

In case of utilizing, as an antenna, at least part of the first member 530 together with the nonmetallic second member 540 in the segmental portion, the performance of the antenna may be enhanced by insulating at least part of the first member 530. For example, the segmental portion may have the nonmetallic second member 540 for electrically isolating the divided segments of the first member 530 from each other. Namely, the side surface F3 of the housing may include at least one second member 540 which divides the first member 530 into at least two segments and insulates the two divided segments of the first member 530 from each other. For example, if the first member 530 is a metallic member such as copper, silver or aluminum, the first member 530 may be partly isolated by an insulating member such as synthetic resin of the second member 540.

According to various embodiments of the present disclosure, through an injection molding process, the second member 540 may be located in the segmental portion which divides the first member 530 into at least two segments. For example, the second member 540 may be located in the segmental portion by injecting a nonmetallic material into a mold, curing the injected nonmetallic material, and then combining the cured nonmetallic material with the first member 430 formed of a metallic material. The second member 540 may use a nonmetallic material such as acrylonitrile-butadien-styrene blend (ABS), polycarbonate (PC), polyoxymethylene (POM, also known as acetal resin) glass, or any other plastic polymer or resin. This is exemplary only, and any other member or material capable of insulating the first member 530 may be used alternatively.

According to various embodiments of the present disclosure, the electronic device may include a sensor located in a housing inner space adjacent to the segmental portion and also oriented to detect incident light received from the outside. In this case, the second member 540 included in the segmental portion may be formed of a transparent material such as glass or synthetic resin such as transparent acryl. Also, the second member 540 included in the segmental portion may be formed of a toned translucent material.

According to various embodiments of the present disclosure, the sensor may be oriented to detect incident light received from the outside through the segmental portion, disposed in the electronic device, and electrically connected with a PCB and/or a flexible PCB (FPCB).

According to various embodiments of the present disclosure, the sensor can receive a ray(s) of light from the outside and then converts the received light ray(s) into an electric signal. In this case, the light ray(s) refers to an electromagnetic wave having a specific wavelength such as an infrared ray, a visible ray, and the like. The sensor may be mounted at a certain position corresponding to the segmental portion. The sensor may be at least one of a luminance sensor, a photoplethysmoraphy (PPG) sensor, an infrared (IR) sensor, and an ultraviolet (UV) sensor. The sensor may include, for example, a sensor thin film transistor, a switch thin film transistor, and a storage condenser. The sensor thin film transistor may output an electric current created by an incident light ray when exposed to light, the storage condenser may accumulate electric charges of such electric currents and also convert the charges into a certain voltage, and the switch thin film transistor may output the voltage in accordance with a gate-on signal.

Figure 6:
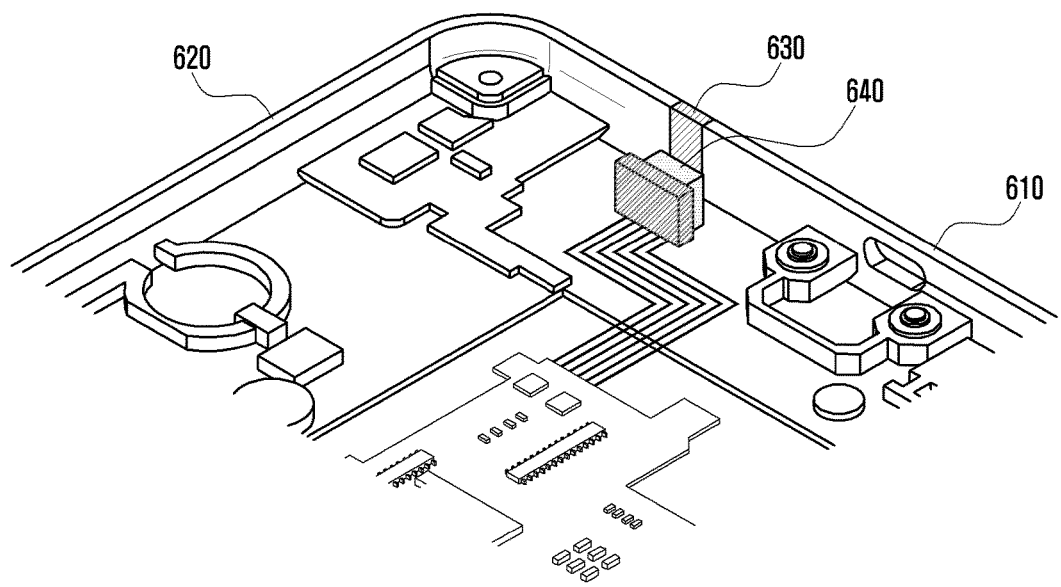
FIG. 6 is a perspective view partially illustrating an electronic device having a sensor disposed therein to detect incident light through a segmental portion according to various embodiments of the present disclosure.

FIG. 6 is a perspective view partially illustrating an electronic device having a sensor disposed therein to detect incident light through a segmental portion according to various embodiments.

According to various embodiments, the electronic device 400 may include a sensor 640 located in an inner space adjacent to a segmental portion 630 and oriented to detect incident light received from the outside through the segmental portion 630.

Referring to FIG. 6, the segmental portion 630 may include a second member between a first member 610 which receives different frequency bands or identical frequency band and the other first member 620. A sensor 640 may be located in an internal space adjacent to the segmental portion 630 and mounted to be oriented to detect the incident light.

According to various embodiments of the present disclosure, the second member included in the segmental portion 630 may be formed of a transparent material such as glass or synthetic resin, e.g., transparent acryl such that the sensor 640 can detect an incident light ray received through the segmental portion 630. Also, the second member included in the segmental portion 630 may be formed of a toned translucent material. In case of using such a toned translucent material as the second member, the intensity of the received light ray may be reduced in comparison with case of using a transparent material as the second member. However, since the capability of sensing may be adjusted through a technique to regulate the sensitivity of the sensor or any other suitable technique, the sensor may detect incident light even when a toned translucent material is used as the second member.

According to various embodiments of the present disclosure, the sensor 640 receives a ray of light from the outside and then converts the received light ray into an electric signal. This light ray comprises an electromagnetic wave having a specific wavelength such as an infrared ray, a visible ray, and the like. The sensor 640 may be mounted at a certain position corresponding to the second member so as to detect incident light through the second member. The sensor 640 may comprise at least one of a luminance sensor, a photoplethysmoraphy (PPG) sensor, an infrared (IR) sensor, and an ultraviolet (UV) sensor.

In a certain embodiment, a light-receiving unit of the sensor 640 may have a size which is different from the size of the segmental portion. In this case, the segmental portion may have a concave or convex lens structure such that the light-receiving unit of the sensor 640 can receive light equally.

In a certain embodiment, the light-receiving unit may have the same size as that of the segmental portion 630. In this case, the segmental portion may have a simple structure for allowing the passage of light or a micro-hole structure.

In a certain embodiment, at least part of the sensor 640 may be included in the segmental portion 630. For example, if the light-receiving unit of the sensor 630 is contained partly or wholly within the segmental portion 630, the light-receiving unit can receive light equally without a need to form the segmental portion in a concave or convex shape.

According to various embodiments, the electronic device 400 may include a processor electrically connected with the display and the at least one sensor 640.

According to a certain embodiment, the electronic device 400 may include a communication circuit electrically connected with at least part of a first elongated member, which may refer to at least one of segments divided from the first member 430.

Figure 7A:
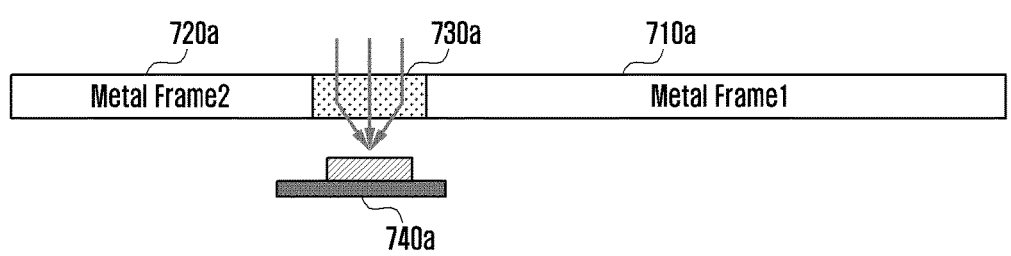
FIG. 7A, FIG. 7B and FIG. 7C are schematic diagrams illustrating various examples of the segmental portion shown in FIG. 6 of the present disclosure.
Figure 7B:
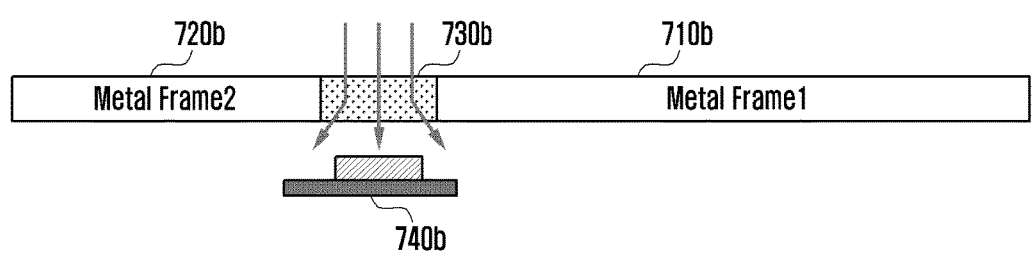
Figure 7C:
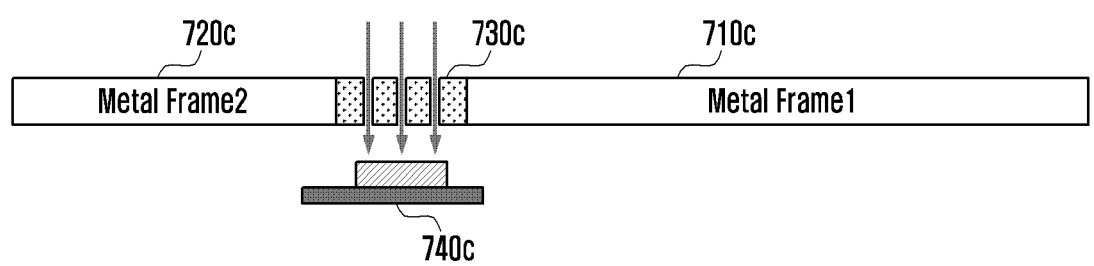

FIGS. 7A to 7C are schematic diagrams illustrating various examples of the segmental portion shown in FIG. 6.

FIG. 7A shows a segmental portion 730a formed in a concentrating structure. Referring to FIG. 7A, the segmental portion 730a may be located between a first member 710a and another first member 720a both of which are configured to receive different frequency bands. A second member may indicate the segmental portion 730a or be located in the segmental portion 730a. A sensor 740a may be mounted so as to correspond to the location of the segmental portion 730a. The sensor 740a as shown in FIG. 7A may detect light concentrated through the segmental portion 730a formed in a concentrating structure. This structure may be used when the second member located in the segmental portion 730a has a greater width than that of the light-receiving unit of the sensor 740a. In addition, this structure may enhance the performance of the sensor 740a by concentrating incident light rays onto the light-receiving unit of the sensor 740a through the segmental portion 730*a*. The segmental portion 730*a* formed in a concentrating structure may include a convex lens.

FIG. 7B shows a segmental portion 730*b* formed in a spectral structure. Referring to FIG. 7B, the segmental portion 730*b* may be located between a first member 710*b*, and another first member 720*b*, both of which are configured to receive different frequency bands. A second member may indicate the segmental portion 730*b* or be located in the segmental portion 730*b*. A sensor 740*b* may be mounted so as to correspond to the location of the segmental portion 730*b*. The sensor 740*b* as shown in FIG. 7B may detect light distributed through the segmental portion formed in a spectral structure. This structure may be used when the second member located in the segmental portion 730*b* has a smaller width than that of the light-receiving unit of the sensor 740*b*. In addition, this structure may enhance the performance of the sensor 740*b* by equally delivering incident light rays to the light-receiving unit of the sensor 740*b* through the segmental portion 730*b*. The segmental portion 730*b* formed in a spectral structure may include a concave lens.

FIG. 7C shows a segmental portion 730*c* formed in a direct-incident structure including a plurality of micro-holes. Referring to FIG. 7C, the segmental portion 730*c* may be located between a first member 710*c* and another first member 720*c*, both of which are configured to receive different frequency bands. A second member may indicate the segmental portion 730*c*, or be located in the segmental portion 730*c*. A sensor 740*c* may be mounted so as to correspond to the location of the segmental portion 730*c*. The sensor 740*c* as shown in FIG. 7C may detect light received directly through the segmental portion formed in a direct-incident structure having micro-holes.

According to various embodiments of the present disclosure, the segmental portion 730*c* may include at least one micro-hole which may have various sizes. This micro-hole may refer to a smaller-sized hole less than a 0.1 mm diameter. Such a smaller-sized micro-hole may be advantageous to a better design of the housing. In view of both a light sensibility and a housing design, the micro-hole may have a diameter ranging from 0.03 mm to 0.05 mm. In case of a micro-hole having a diameter less than 0.03 mm, the sensor may fail to detect light. Therefore, a micro-hole having a diameter of 0.03 mm or more is desirable. On the other hand, a micro-hole having a diameter less than 0.05 mm may be desirable such that a user cannot visually distinguish such micro-holes from the other region having no micro-hole.

According to various embodiments of the present disclosure, the segmental portion may have a pattern of micro-holes. For example, the pattern of micro-holes may represent a figure, a picture, a symbol, or the like. A wider gap between such micro-holes may be advantageous to a better design of the housing. However, since a considerably wider gap may degrade a light-receiving rate, a suitable gap should be determined in view of a light-receiving rate. Experimentally, it was shown that it is desirable to form a gap between micro-holes about twice the diameter of a micro-hole, i.e., from 0.05 mm to 0.01 mm, in view of a housing design as well as a light-receiving rate.

Figure 8A:
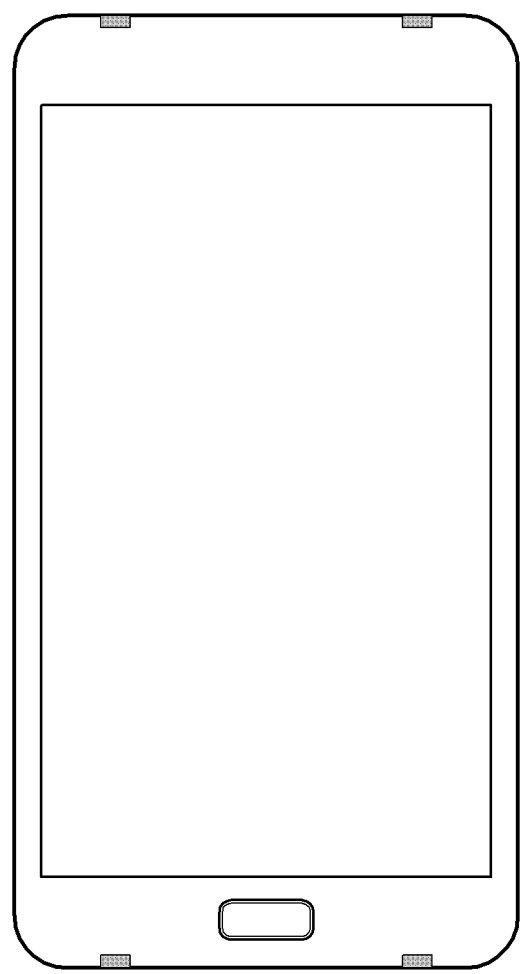
FIG. 8A, FIG. 8B, FIG. 8C and FIG. 8D are plan views illustrating various arrangements of segmental portions according to various embodiments of the present disclosure.
Figure 8B:
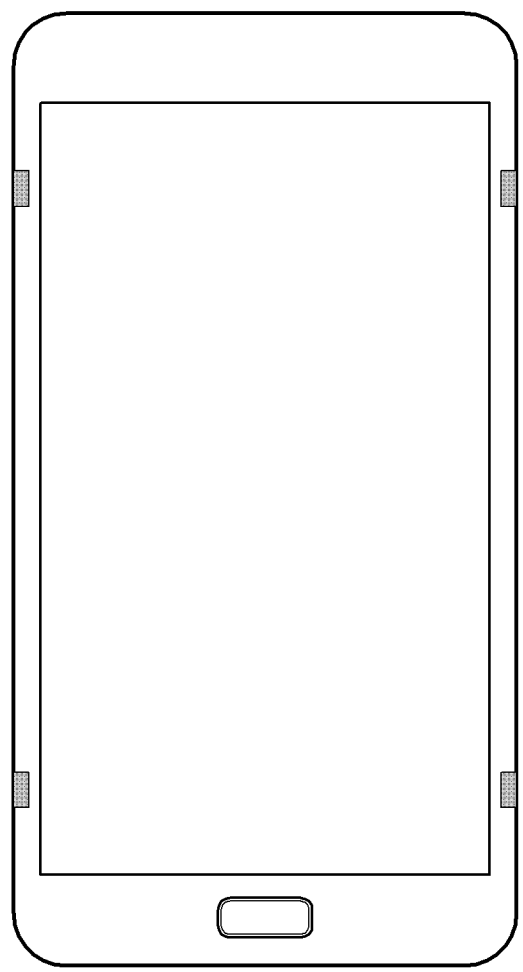
Figure 8C:
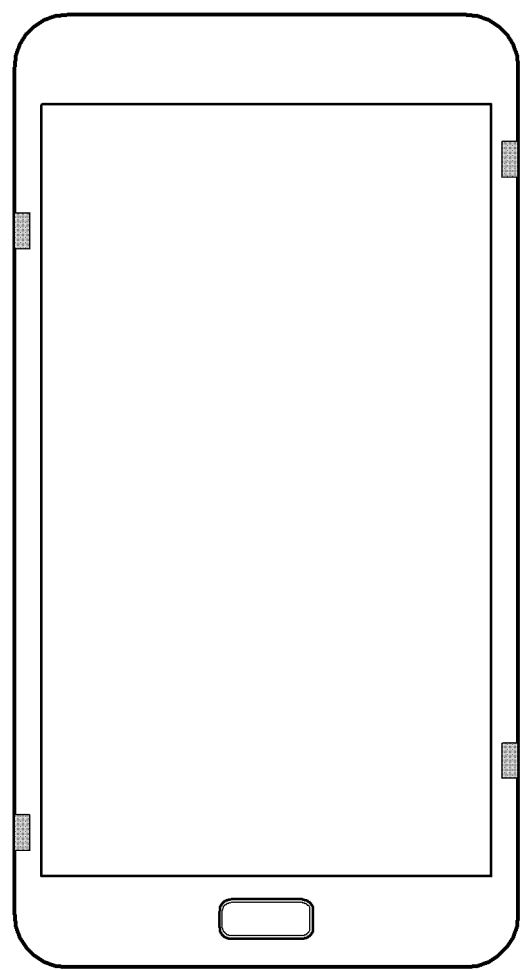
Figure 8D:
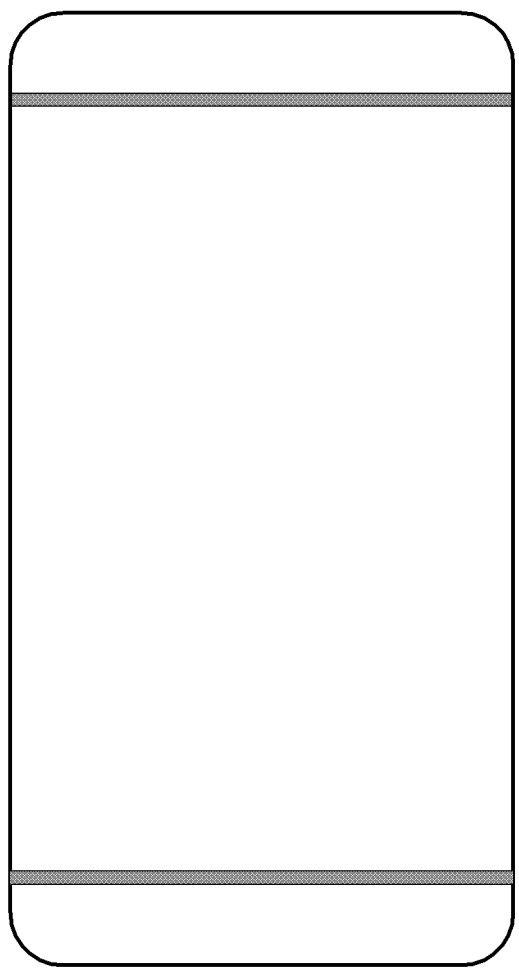

FIGS. 8A to 8C are plan views illustrating segmental portions arranged on a side surface according to various embodiments. FIG. 8D is a plan view illustrating segmental portions arranged on a back surface according to various embodiments.

Referring to FIGS. 8A to 8C, shown are examples of four segmental portions arranged on the side surface of the housing. This is, however, exemplary only and not to be construed as a limitation. Alternatively, more or less segmental portions can be arranged on the side surface of the housing.

In FIG. 8A, four segmental portions are arranged on upper and lower side surfaces of the electronic device in a symmetric form. Although not shown, an asymmetric arrangement is also possible. In FIG. 8B, four segmental portions are arranged symmetrically on left and right side surfaces of the electronic device. In FIG. 8C, four segmental portions are arranged asymmetrically on left and right side surfaces of the electronic device.

Referring now to FIG. 8D, shown is an example of two segmental portions respectively arranged on the second surface F2 of the housing. For example, each segmental portion shown in FIG. 8D may be a part, extended to the second surface F2, of the segmental portion shown in FIG. 8B. Also, in a certain embodiment, the second and side surfaces F2 and F3 of the electronic device 400 may be formed to have an unclear boundary, so that the segmental portion partially included in the side surface F3 may be extended to the second surface F2. Although in FIG. 8D the segmental portions are shown in the form of two parallel lines, the present claims are not limited to such an arrangement, as the location, number and/or shape of the segmental portions may be varied depending on the segmental portions included in the side surface.

Figure 9A:
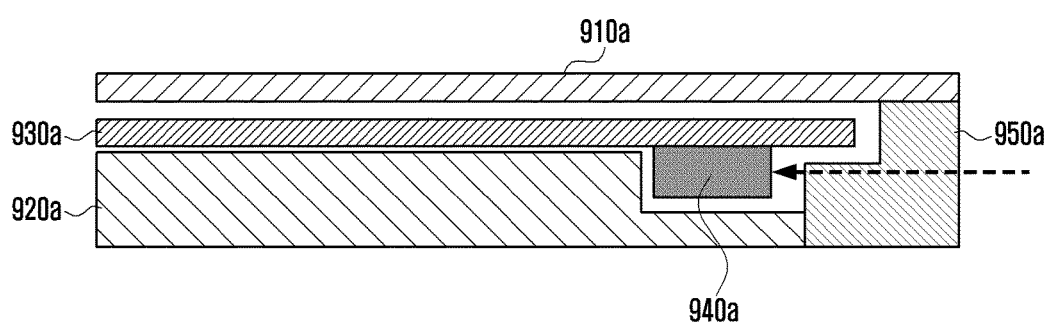
FIG. 9A and FIG. 9B are cross-sectional views illustrating mounting structures of a sensor according to various embodiments of the present disclosure.
Figure 9B:
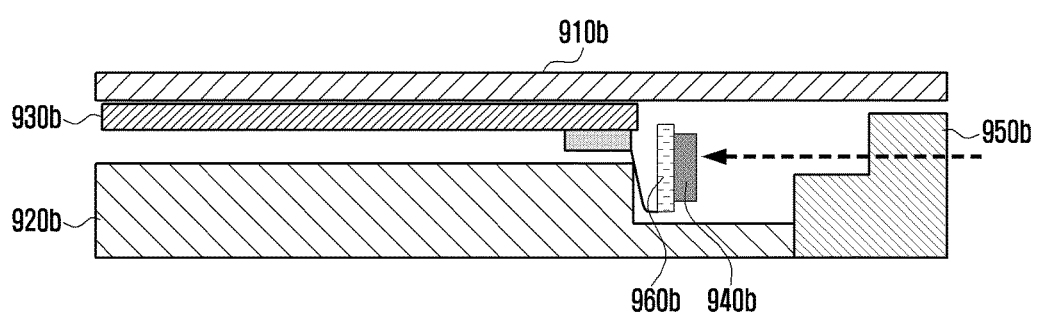

FIGS. 9A and 9B are cross-sectional views illustrating mounting structures of a sensor according to various embodiments.

According to various embodiments of the present disclosure, a sensor for detecting incident light may be mounted on a PCB or FPCB in various manners depending on a light detection direction. This PCB or FPCB may mechanically support the sensor and electrically connect the sensor and a processor through wiring patterns formed thereon.

FIG. 9A shows a mounting structure of a sensor 940*a* that detects incident light in a lateral direction thereof. The sensor 940*a* may be electrically connected with one of a PCB and an FPCB. As shown in FIG. 9A, the PCB 930*a* may be located between a display 910*a* included at least partly in the first surface F1 and a housing 920*a* included at least partly in the second part F2, running in parallel with them. In this case, the sensor 940*a* may be directly mounted on the PCB 930*a* such that the light-receiving unit thereof may orient toward the direction of incident light. For example, the sensor 940*a* may be directly attached onto the PCB 930*a* so as to detect incident light received through a segmental portion 950*a*.

FIG. 9B shows a mounting structure of a sensor 940*b* that detects incident light in a front or rear direction thereof. As shown in FIG. 9B, a PCB 930*b* may be located between a display 910*b* included at least partly in the first surface F1 and a housing 920*b* included at least partly in the second part F2, running in parallel with them. In this case, the sensor 940*b* may fail to be directly mounted on the PCB 930*b* since the sensor 940*b* detects incident light in a front direction thereof. Therefore, an FPCB 960*b* electrically connected with the PCB 930*b* may be used for supporting the sensor 930*b*. In this case, the sensor 930*b* may be directly mounted on the FPCB 960*b* such that the light-receiving unit thereof may orient toward the direction of incident light. For example, the sensor 940*b* may be directly attached onto the FPCB 960*b* so as to detect incident light received through a segmental portion 950*b*.

Although the segmental portions 950*a* and 950*b* are shown as having an L-like shape in FIGS. 9A and 9B, any other form may be also possible. For example, the segmental portion may have a straight shape or a curved shape.

Although not shown in FIGS. 9A and 9B, the segmental portion 950a or 950b may be formed in intaglio to accommodate at least part of the sensor. For example, if the light-receiving unit of the sensor has a smaller size than that of the segmental portion, the light-receiving unit of the sensor may be contained at least partly in the segmental portion.

Figure 10A:
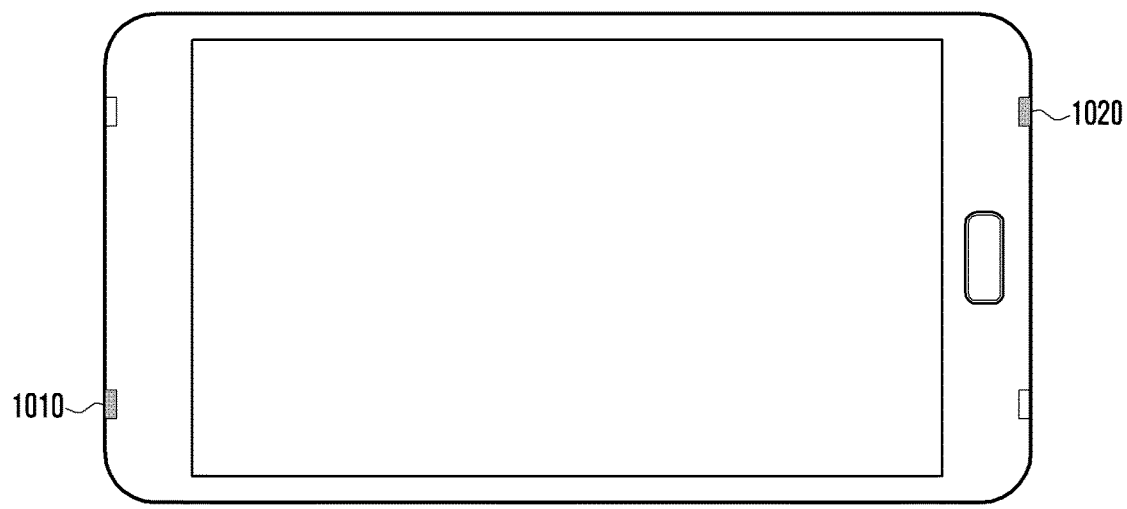
FIG. 10A is a plan view illustrating optical sensors selectively equipped in segmental portions of an electronic device.

FIG. 10A is a plan view illustrating optical sensors selectively equipped in segmental portions of an electronic device.

According to various embodiments, a sensor located in a housing inner space adjacent to a segmental portion and oriented to detect incident light through the segmental portion may be a luminance sensor. Normally, the luminance sensor may be used to receive surrounding light and measure ambient brightness. For example, the luminance sensor may be used to adjust the brightness of a display depending on ambient brightness. Therefore, the luminance sensor is disposed adjacent to the display. Due to the luminance sensor typically located near an upper part of the electronic device, the luminance sensor may often fail to measure ambient brightness flexibly depending on the state of the electronic device.

FIG. 10A shows an electronic device having at least four segmental portions. Among them, a first segmental portion 1010 and a second segmental portion 1020 may include a luminance sensor.

Namely, the electronic device including at least four segmental portions may recognize a state thereof by means of the luminance sensors contained in the first and second segmental portions 1010 and 1020 and then measure ambient brightness flexibly depending on the recognized state.

Figure 10B:
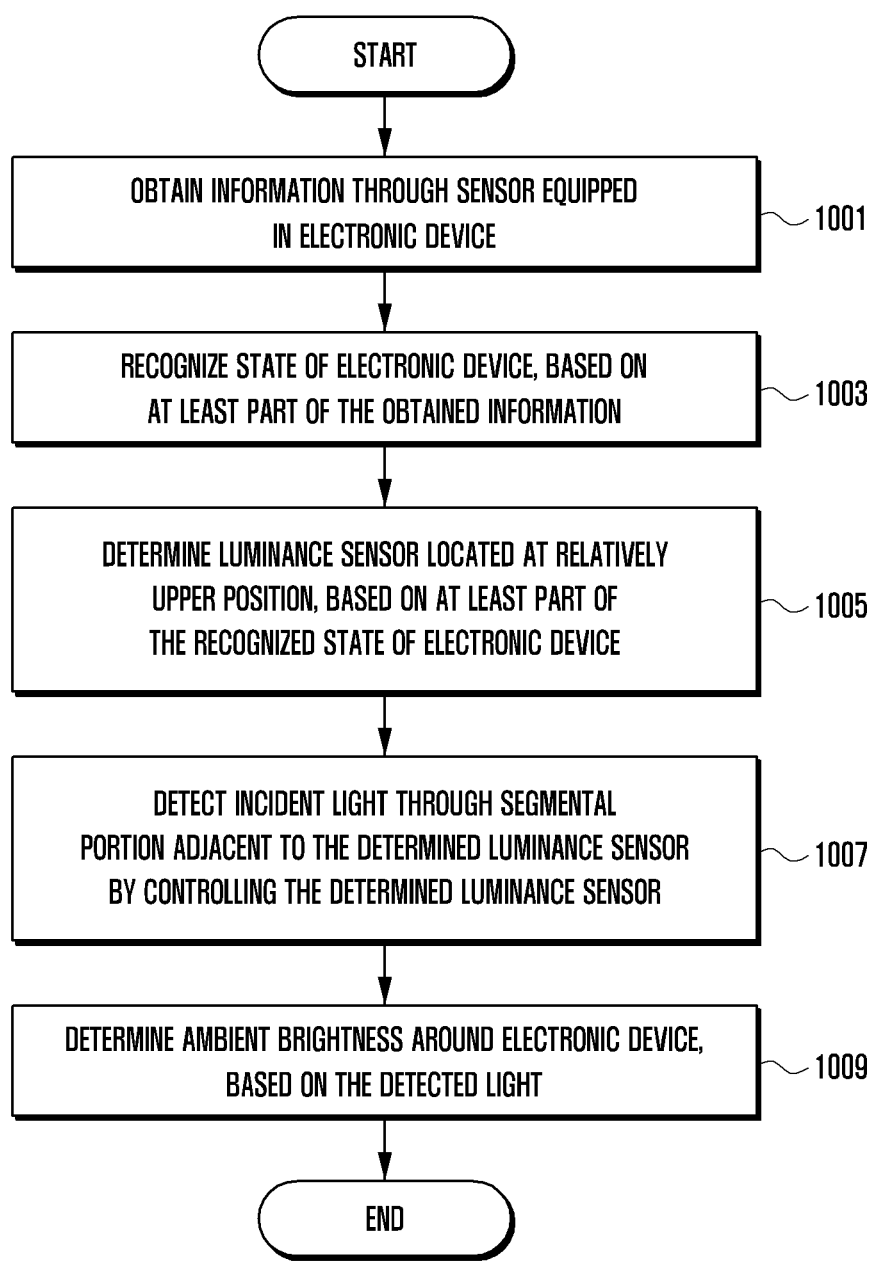
FIG. 10B is a flow diagram illustrating a method for measuring ambient brightness flexibly depending on a state of an electronic device.

FIG. 10B is a flow diagram illustrating a method for measuring ambient brightness flexibly depending on a state of an electronic device.

Referring to FIG. 10B, at operation 1001, the electronic device 400 may obtain information through a sensor equipped therein. For example, the electronic device 400 may obtain information about an angular velocity thereof through the gyro sensor 240B. In addition, the electronic device 400 may obtain information about acceleration thereof through the acceleration sensor 240E.

At operation 1003, the electronic device 400 may recognize the state thereof, based on at least part of the obtained information. For example, in case of obtaining information about an angular velocity through the gyro sensor 240E, the electronic device 400 may recognize the state thereof, based on the obtained angular velocity information. The state of the electronic device 400 may refer to a tilted degree of the electronic device 400 and/or a facing direction of the display.

At operation 1005, based on at least part of the recognized state of the electronic device 400, the electronic device 400 may determine a luminance sensor located at a relatively upper position. For example, if the first segmental portion 1010 is located at a relatively upper position than the second segmental portion 1020 in the electronic device 400 as shown in FIG. 10A, the electronic device 400 may determine a luminance sensor disposed adjacent to the first segmental portion 1010 as an upper luminance sensor. Similarly, if the second segmental portion 1020 is located at a relatively upper position than the first segmental portion 1010 in the electronic device 400, the electronic device 400 may determine a luminance sensor disposed adjacent to the second segmental portion 1020 as an upper luminance sensor.

In a certain embodiment, at least two luminance sensors located at upper positions may be determined. For example, in the electronic device having two or more luminance sensors, at least two upper luminance sensors may be determined when at least two luminance sensors are equally apart from the bottom or when it is predefined to determine at least two luminance sensors for measuring ambient brightness.

At operation 1007, the electronic device 400 may control the determined luminance sensor to detect incident light through the segmental portion adjacent to the determined luminance sensor. For example, if a luminance sensor disposed adjacent to the first segmental portion 1010 is determined as an upper luminance sensor in the electronic device 400 as shown in FIG. 10A, the determined luminance sensor may be activated to detect incident light through the first segmental portion 1010.

In a certain embodiment, if two or more luminance sensors for measuring ambient brightness are determined, the ambient brightness around the electronic device 400 may be measured by using the determined two or more luminance sensors. In a certain embodiment, the electronic device 40 may recognize that the display thereof faces toward the floor. In this case, the electronic device 400 may disallow the operation of all luminance sensors or control luminance sensors adjacent to the first or second segmental portion 1010 or 1020 to operate.

At operation 1009, based on the detected light, the electronic device 400 may determine ambient brightness around the electronic device 400. Therefore, based on the determined ambient brightness, the electronic device 400 may control the brightness of the display, or the like.

As discussed hereinbefore, using two or more luminance sensors included in the segmental portions, it is possible to exactly measure the ambient brightness around the electronic device.

According to various embodiments of this disclosure, an operating method of the electronic device having at least one segmental portion may include operation of obtaining information through a sensor equipped in the electronic device, operation of recognizing a state of the electronic device, based on at least part of the obtained information, operation of determining (i.e. identifying the presence of) a luminance sensor located at a relatively upper position, based on at least part of the recognized state of the electronic device, operation of detecting incident light through the segmental portion adjacent to the determined luminance sensor by controlling the determined luminance sensor, and operation of determining ambient brightness around the electronic device, based on the detected light.

According to various embodiments of this disclosure, the above method may further include, if it is recognized that a display of the electronic device faces toward a floor, operation of inactivating all luminance sensors or activating at least two luminance sensors.

Although not shown in the drawings, the electronic device may have a photo-plethysmography (PPG) sensor located in a housing inner space adjacent to the segmental portion. The PPG sensor is a device that senses a blood flow by passing through light and thereby detects a heart rate. In case a user touches the second member with his or her finger, the PPG sensor may check a current heart rate and output it on the display. Typically, when a user's finger is placed on the segmental portion, the PPG sensor adjacent to the segmental portion emits rays of light (e.g., infrared rays) toward the finger. The emitted rays of light pass through several media of the finger and spread widely. Then some of the rays of light are detected by the PPG sensor. Since the PPG sensor is well known in the art, a detailed description will be omitted.

According to various embodiments of the present disclosure, an electronic device may comprise a housing, a display, at least one sensor, and a processor. The housing may include a first surface, a second surface being opposite to the first surface, and a side surface enclosing at least part of a space formed between the first and second surfaces. In this housing, the side surface may include a first member elongated along the side surface and formed of an opaque material, and at least one second member dividing the first member into at least two segments and formed of a light-transmittable material. The display may be exposed on the first surface. The at least one sensor may be located in the space adjacent to the at least one second member and oriented to detect incident light received through the at least one second member. The processor may be electrically connected with the display and the sensor.

According to various embodiments of this disclosure, the electronic device may further comprise a communication circuit electrically connected with at least part of the first member wherein the first element includes a metallic material.

According to various embodiments of this disclosure, the second member may be formed in at least one of a concentrating structure, a spectral structure, and a direct-incident structure including a plurality of micro-holes.

According to various embodiments of this disclosure, if the second member is formed in the direct-incident structure including the plurality of micro-holes, each of the micro-holes may have a diameter ranging from 0.03 mm to 0.05 mm.

According to various embodiments of this disclosure, the sensor may include at least one of a luminance sensor, a photoplethysmoraphy (PPG) sensor, an infrared (IR) sensor, and an ultraviolet (UV) sensor.

According to various embodiments of this disclosure, the at least one second member may include at least two second members spaced apart from each other, and each of the at least two second members may divide the first member into two segments.

According to various embodiments of this disclosure, the at least one sensor may include at least two sensors each of which is located in the space adjacent to each of the at least two second members and oriented to detect incident light received through each of the at least two second members.

According to various embodiments of this disclosure, the display exposed on the first surface may be a flexible display.

According to various embodiments of this disclosure, the first member may include a metallic material having ductility.

According to various embodiments of this disclosure, the electronic device may further comprise another housing including another first surface, another second surface being opposite to the another first surface, and another side surface enclosing at least part of a space formed between the another first and second surfaces, wherein the housing and the another housing are combined with each other directly or indirectly.

According to various embodiments of the present disclosure, the another side surface may include a third member elongated along the another side surface and formed of an opaque material, and at least one fourth member dividing the third member into at least two segments and formed of a light-transmittable material.

According to various embodiments of the present disclosure, the at least one second member may be extended along the second surface and connected with another second member included in the side surface.

Figure 11:
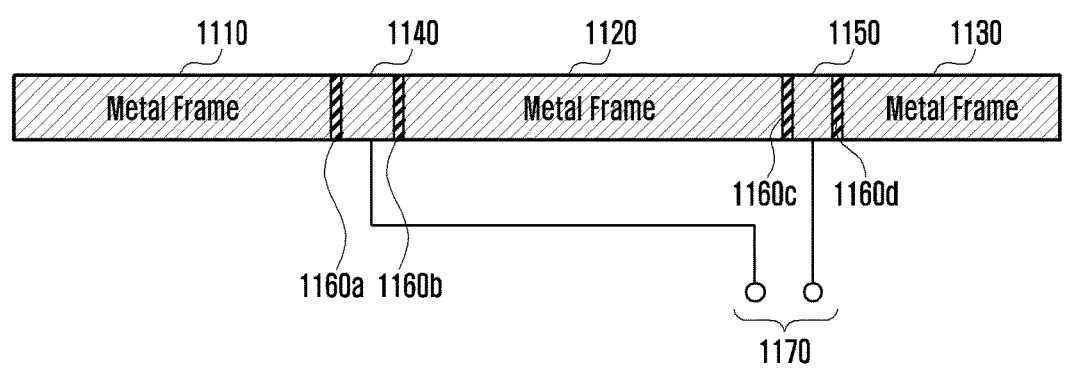
FIG. 11 is a schematic diagram illustrating an electronic device using at least one segmental portion as an electrode.

FIG. 11 is a schematic diagram illustrating an electronic device using at least one segmental portion as an electrode.

According to various embodiments of the present disclosure, the side surface F3 of the housing may include a first member elongated along the side surface F3 and divided into two segments, a second member formed of a metallic material and located between the two segments of the first member, a third member for electrically isolating one of the two segments of the first member from the second member, and a fourth member for electrically isolating the other of the two segments of the first member from the second member.

Referring now to FIG. 11, the first member elongated along the side surface F3 of the housing may be divided into a first segment 1110 and a second segment 1120. The second member 1140 may be located between the first and second segments 1110 and 1120. The second member 1140 is a metallic member in order to provide an electrode function.

In order to use the housing of the electronic device as an antenna, the first member may be a metallic member formed of copper, silver, aluminum, or the like. In this particular embodiment, the second member is also a metallic member. With such construction, it is therefore required to electrically isolate the first member from the second member. For this reason, as shown in FIG. 11, a third member 1160a may be used for an electrical isolation between the first segment 1110 and the second member 1140. Also, a fourth member 1160b may be used for an electrical isolation between the second segment 1120 and the second member 1140. The third and fourth members 1160a and 1160b may be formed of an insulating material such as glass, ebonite, diamond, rubber, or the like.

According to various embodiments of the present disclosure, the electronic device may include at least two second members used as an electrode. Referring to FIG. 11, the first member may be divided into the first, second and third segments 1110, 1120 and 1130. Then the second members 1140 and 1150 may be disposed between the first and second segments 1110 and 1120 and between the second and third segments 1120 and 1130, respectively. Each of the second members 1140 and 1150 may be metallic members suitable for being used as an electrode.

In an embodiment of the present disclosure, another third member 1160c may be used for an electrical isolation between the second segment 1110 and another second member 1150. Also, another fourth member 1160d may be used for an electrical isolation between the third segment 1130 and another second member 1150. These third and fourth members 1160c and may be formed of an insulating material such as glass, ebonite, diamond, rubber, or the like.

In FIG. 11, the second members 1140 and 1150 used as electrodes may be located in an inner space of the electronic device and electrically connected with a biometric sensor 1170 which is also electrically connected with the second members 1140 and 1150. For example, the biometric sensor 1170 may include at least one of an electrocardiogram sensor, a galvanic skin reflex (GSR) sensor, a grip sensor, and a fingerprint sensor.

According to a certain embodiment, the second member for an electrode may be used as an input terminal based on a difference in capacitance. In this case, the second member may operate as a secondary key or a security key, e.g., a camera shutter, a fingerprint sensor, or the like.

According to various embodiments, the electronic device 400 may include a processor electrically connected with the display and the biometric sensor 1170.

According to a certain embodiment, the electronic device 400 may include a communication circuit electrically connected with at least part of the first elongated member, which may refer to at least one of segments divided from the first member 430.

Although the electronic device shown in FIG. 11 has two second members used as an electrode, this is exemplary only and not to be considered as a limitation. Alternatively, more or less second members are possible. These second members may be disposed at various locations on the side surface. For example, as discussed earlier in FIGS. 8A and 8B, the second members may be disposed in a symmetric or asymmetric arrangement.

Figure 12A:
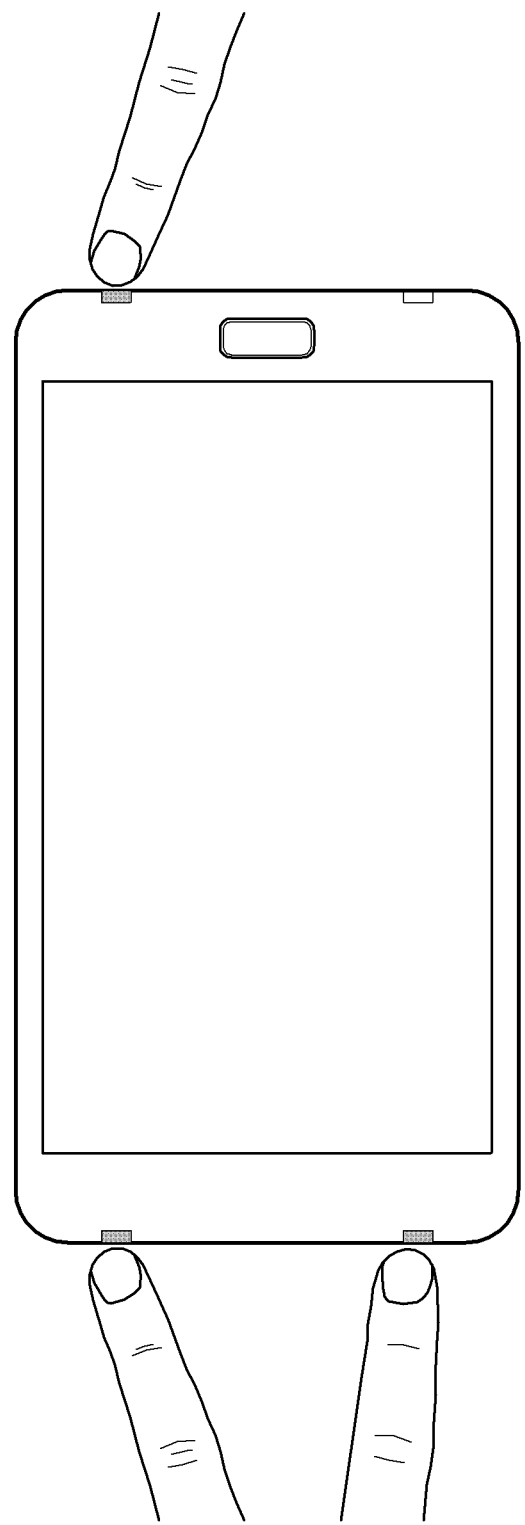
FIG. 12A and FIG. 12B are plan views illustrating examples of using the second member as an electrode.
Figure 12B:
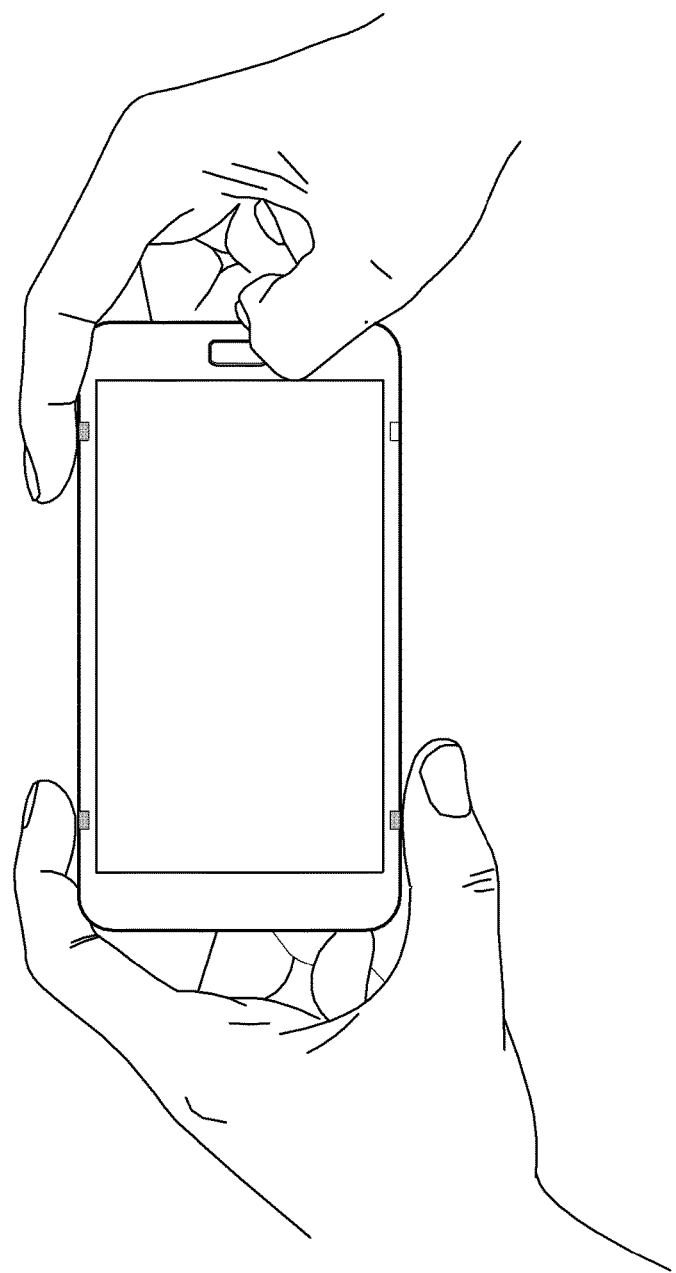

FIGS. 12A and 12B are plan views illustrating examples of using the second member as an electrode.

According to embodiments, the biometric sensor electrically connected with the second member may be an electrocardiogram (ECG) sensor. The ECG sensor refers to a device capable of measuring an action current caused by dilation and constriction of heart muscle through an external electrode. An action potential created by dilation and constriction of heart muscle causes an electric current spreading from the heart to the whole body, and this current produces a potential difference depending on body positions. The ECG sensor may detect such a potential difference through a surface electrode attached to the skin.

According to embodiments, the biometric sensor electrically connected with the second member may be a galvanic skin reflex (GSR) sensor. The GSR sensor may measure GSR by measuring conductivity of the skin. Specifically, a strong feeling stimulates the sympathetic nervous system and secretes a lot of sweat from the sweat gland, so that this phenomenon may allow measuring GSR through electrodes attached to two fingers.

According to embodiments of the present disclosure, at least two electrodes are needed to measure GSR, and a plurality of electrodes, e.g., three or more electrodes, are needed to measure an ECG signal.

Referring now to FIGS. 12A and 12B, shown are examples of using three or more second members used as electrodes for measuring ECG and GSR. For example, in case of measuring ECG, a user may touch his or her skin (e.g., fingers) to three or more second members used as electrodes. FIG. 12A shows an example of measuring ECG through the second members disposed symmetrically on upper and lower sides of the electronic device, and FIG. 12B shows an example of measuring ECG through the second members disposed symmetrically on left and right sides of the electronic device. Although not shown, the second members disposed asymmetrically may be also used for measuring ECG.

Figure 13:
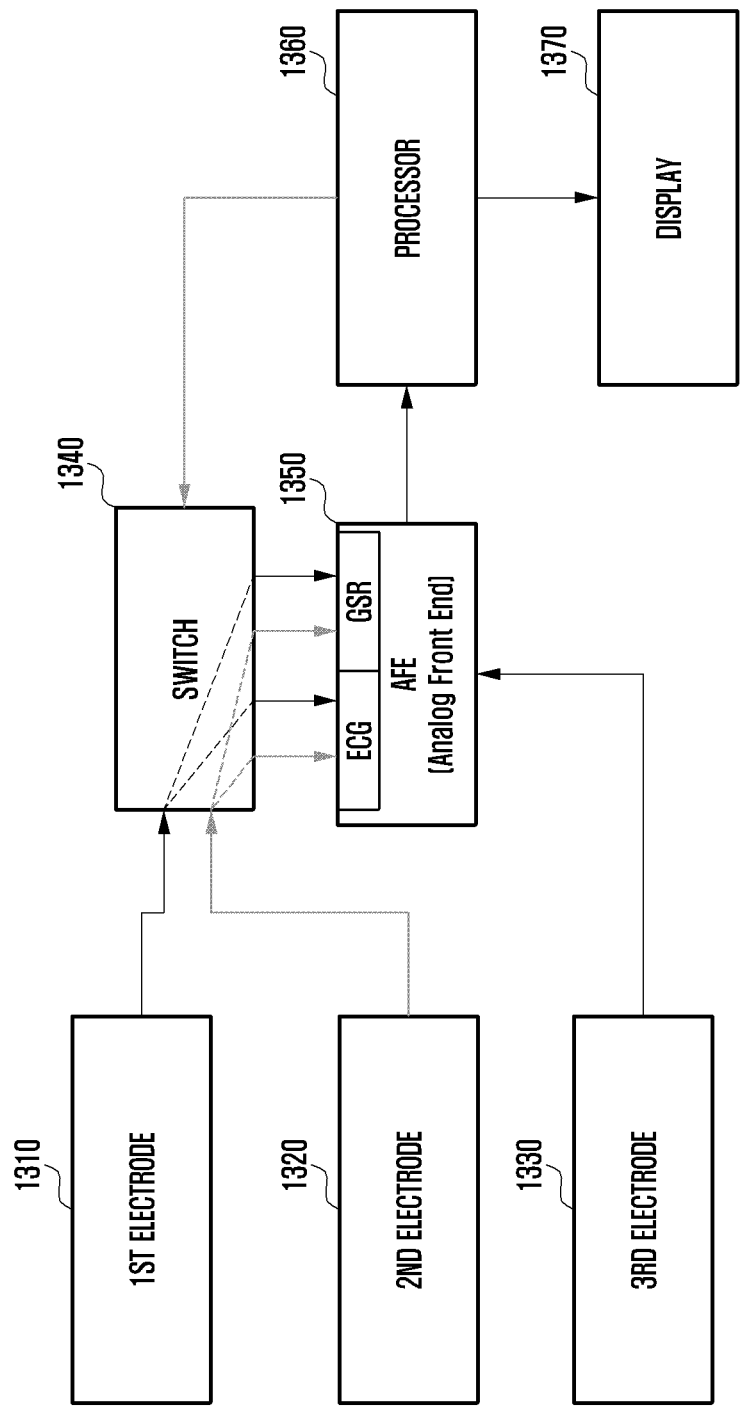
FIG. 13 is a block diagram illustrating an electronic device according to various embodiments of the present disclosure.

FIG. 13 is a block diagram illustrating an electronic device according to various embodiments.

Referring to FIG. 13, in order to measure GSR or ECG by using three or more second members used as electrodes, the electronic device may include a first electrode 1310, a second electrode 1320, a third electrode 1330, a switch 1340, an analog front end (AFE) 1350, a processor 1360, and a display 1370.

According to various embodiments of the present disclosure, in case of measuring GSR, the electronic device 400 may use only the first and second electrodes 1310 and 1320. Contrary to this, in case of measuring ECG, the electronic device 400 may use all of first, second and third electrodes 1310, 1320 and 1330. According to various embodiments, the electronic device 400 may recognize whether a GSR measurement or an ECG measurement and then control the switch 1340. For example, if the processor 1360 recognizes the measurement of GSR, the switch 1340 may control a delivery of signals from the first and second electrodes 1310 and 1320 to a GSR part of the AFE 1350. In another example, if the processor 1360 recognizes the measurement of ECG; the switch 1340 may control a delivery of signals from the first and second electrodes 1310 and 1320 to an ECG part of the AFE 1350. Further, in case of this ECG measurement requiring three or more electrodes, the third electrode 1330 may be connected directly with the ECG AFE 1350.

According to various embodiments of the present disclosure, the AFE 1350 which is a pre-processing circuit for a signal measurement includes a frequency band filter, an amplifier, and an analog-digital converter (ADC). The AEF 1350 receives a bio-signal from each electrode and then pre-processes such signals for a predetermined measurement. For example, the ECG AFE 1350 may pre-process signals for the ECG measurement, and the GSR AFE 1350 may pre-process signals for the GSR measurement. Since the AFE is well known in the art, a detailed description will be omitted.

The processor 1360 receives the pre-processed signals from the AFE 1350 and then performs particular operations in accordance with predetermined instructions. For example, the processor 1360 may control the display 1370 to display the measured ECG or to display a result of using the GSR measurement as a lie detector.

According to various embodiments of the present disclosure, an electronic device may comprise a housing, a display, a biometric sensor, and a processor. The housing may include a first surface, a second surface being opposite to the first surface, and a side surface enclosing at least part of a space formed between the first and second surfaces. The side surface may include a first member elongated along the side surface and divided into segments, a second member formed of a metallic material and located between the segments of the first member, a third member for electrically isolating one of the segments of the first member from the second member, and a fourth member for electrically isolating the other of the segments of the first member from the second member. The display may be exposed on the first surface. The biometric sensor may be located in the space and electrically connected with the second member. The processor may be electrically connected with the display and the biometric sensor.

According to various embodiments of the present disclosure, the electronic device may further comprise a communication circuit electrically connected with at least part of the first member wherein the first element includes a metallic material.

According to various embodiments of the present disclosure, the side surface may include the first member elongated along the side surface and divided into at least three segments; at least two second members each of which is formed of a metallic material and located between the adjacent segments of the first member; at least two third member each of which electrically isolates a corresponding one of the at least two second members from one of the adjacent segments of the first member; and at least two fourth member each of which electrically isolates a corresponding one of the at least two second members from the other of the adjacent segments of the first member.

According to various embodiments of the present disclosure, the biometric sensor may be electrically connected with each of the at least two second members.

According to various embodiments of the present disclosure, the biometric sensor may include at least one of an electrocardiogram sensor, a galvanic skin reflex (GSR) sensor, a grip sensor, and a fingerprint sensor.

According to various embodiments of the present disclosure, the second member may be used as an input terminal based on a difference in capacitance.

The above-described embodiments of the present disclosure can be implemented in hardware, firmware or via the execution of software or computer code that can be stored in a recording medium such as a CD ROM, a Digital Versatile Disc (DVD), a magnetic tape, a RAM, flash, a floppy disk, a hard disk, or a magneto-optical disk or computer code downloaded over a network originally stored on a remote recording medium or a non-transitory machine readable medium and to be stored on a local recording medium, so that the methods described herein can be rendered via such software that is stored on the recording medium using a general purpose computer, or a special processor or in programmable or dedicated hardware, such as one or more general-purpose processors (e.g., ARM-based processors), a Digital Signal Processor (DSP), a Programmable Logic Device (PLD), an Application-Specific Integrated Circuit (ASIC), a Field-Programmable Gate Array (FPGA), a Graphical Processing Unit (GPU), a video card controller, etc. or the programmable hardware include memory components, e.g., RAM, ROM, Flash, etc. that may store or receive software or computer code that when accessed and executed by the computer, processor or hardware implement the processing methods described herein. Any of the functions and steps provided in the Figures may be implemented in hardware, or a combination hardware configured with machine executable code and may be performed in whole or in part within the programmed instructions of a computer. No claim element herein is to be construed under the provisions of 35 U.S.C. 112, sixth paragraph, unless the element is expressly recited using the phrase "means for." In addition, under the broadest reasonable interpretation, the appended claims are statutory subject matter in compliance with 35 U.S.C. § 101.

The embodiments of the present disclosure are merely provided to assist in a comprehensive understanding of the disclosure and not suggestive of claim limitations. Therefore, it should be understood that many variations and modifications of the basic inventive concept herein described will still fall within the spirit and scope of the embodiments of the disclosure as defined in the appended claims.

What is claimed is:

1. An electronic device comprising:
a housing including a first surface, a second surface opposite to the first surface, and a side surface enclosing at least part of a space formed between the first and second surfaces, wherein the side surface includes a first member elongated along the side surface and formed of an opaque material, and at least one second member dividing the first member into at least two segments and formed of a light-transmittable material;
a display arranged on the first surface;
at least one sensor located in the space partially enclosed by the side surface adjacent to the at least one second member, and the at least one sensor is oriented to detect incident light received through the at least one second member;
a communication circuit electrically connected with at least a part of the first member; and
at least one processor electrically connected with the display, the at least one sensor and the communication circuit,
wherein the at least the part of the first member is used as an antenna radiator, and
wherein the at least one second member insulates the at least two segments from each other, and the at least one second member has a smaller width than a width of a light-receiving unit of the at least one sensor.

2. The electronic device of claim 1, wherein at least part of the first member or second member comprises of a metallic material.

3. The electronic device of claim 1, wherein the second member is formed in at least one of a concentrating structure, a spectral structure, and a direct-incident structure including a plurality of micro-holes.

4. The electronic device of claim 3, wherein if the second member is formed in the direct-incident structure including the plurality of micro-holes, each of the micro-holes has a diameter ranging from 0.03 mm to 0.05 mm.

5. The electronic device of claim 1, wherein the at least one sensor includes at least one of a luminance sensor, a photoplethysmoraphy (PPG) sensor, an infrared (IR) sensor, and an ultraviolet (UV) sensor.

6. The electronic device of claim 1, wherein the at least one second member is comprised of at least two second members spaced apart from each other, and each of the at 1 east two second members divides the first member into segments.

7. The electronic device of claim 6, wherein the at least one sensor includes at least two sensors, each sensor is arranged in the space adjacent to each of the at least two second members and each sensor is oriented to detect incident light received through each of the at least two second members.

8. The electronic device of claim 1, wherein the display exposed on the first surface comprises a flexible display.

9. The electronic device of claim 8, wherein the first member includes a metallic material having ductility.

10. The electronic device of claim 1, further comprising:
another housing including another first surface, another second surface opposite to the another first surface, and another side surface enclosing at least part of a space formed between the another first and second surfaces,
wherein the housing and the another housing are combined with each other directly or indirectly.

11. The electronic device of claim 10, wherein the another side surface includes: a third member elongated along the another side surface and formed of an opaque material, and at least one fourth member dividing the third member into at least two segments and formed of a light-transmittable material.

12. The electronic device of claim 1, wherein the at least one second member extends along the second surface and is connected to another second member included in the side surface.

* * * * *